(12) United States Patent
Vivier et al.

(10) Patent No.: US 7,569,666 B2
(45) Date of Patent: Aug. 4, 2009

(54) POLYPEPTIDES ASSOCIATED WITH ACTIVATORY RECEPTORS AND THEIR BIOLOGICAL APPLICATIONS

(75) Inventors: Eric Vivier, Cassis (FR); Alessandro Moretta, Genoa (IT); Lucia Olcese, Genoa (IT); Frédéric Vely, Cassis (FR); Elena Tomasello, Marseilles (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 426 days.

(21) Appl. No.: 10/902,886

(22) Filed: Aug. 2, 2004

(65) Prior Publication Data

US 2005/0130130 A1 Jun. 16, 2005

Related U.S. Application Data

(60) Continuation of application No. 10/645,539, filed on Aug. 22, 2003, now abandoned, which is a division of application No. 09/403,980, filed as application No. PCT/FR98/00883 on Apr. 30, 1998, now abandoned.

(30) Foreign Application Priority Data

Apr. 30, 1997 (FR) .................. 97 05411
Jan. 28, 1998 (FR) .................. 98 00927

(51) Int. Cl.
*C07K 14/00* (2006.01)
*A61K 39/00* (2006.01)
*C12N 15/09* (2006.01)
*G01N 33/567* (2006.01)

(52) U.S. Cl. ............... 530/350; 424/185.1; 435/69.3; 435/7.21

(58) Field of Classification Search ............... None
See application file for complete search history.

(56) References Cited

OTHER PUBLICATIONS

Cambiaggi et al., "The Natural Killer-Related Receptor for HLA-C Expressed on T Cells From CD3+ Lymphoproliferative Disease of Granular Lymphocytes Displays either Inhibitory or Stimulatory Function", Blood, vol. 87, No. 6 (Mar. 15, 1996), pp. 2369-2375.
Mandelboim et al., "Enhancement of Class II-Restricted T Cell Responses by Costimulatory NK Receptors for Class I MHC Proteins", Science, vol. 274, Dec. 20, 1996, pp. 2097-2100.
Blery et al., "Reconstituted killer cell inhibitor receptors for major histocompatibility complex class 1 molecules control mast ell activation induced via immunoreceptor tyrosine-based activation motifs", The Journal of Biological Chemistry, vol. 272, No. 14, Apr. 4, 1997, pp. 8989-8992.
Olcese et al., "Human killer cell activatory receptors for MHC class 1 molecules are included in a multimeric complex expressed by natural killer cells", The Journal of Immunology, vol. 158, No. 11, Jun. 1, 1997, pp. 5083-5086.
Blery et al., J. Biol. Chem. 272(14):8989-8996, 1997.
Marra et al., Database Est. Accession No. AA242315, Mar. 7, 1997.
Marra et al., Database Est. Accession No. W41142, Sep. 11, 1996.
Marra et al., Database Est. Accession No. W88159, Sep. 12, 1998.
Burke et al., Synthesis 1019-1020, 1991.

*Primary Examiner*—Robert Landsman
*Assistant Examiner*—Bruce D Hissong
(74) *Attorney, Agent, or Firm*—Nixon & Vanderhye P.C.

(57) ABSTRACT

The invention concerns novel means for diagnosing, preventing, compensating, treating an abnormal or unwanted functioning of KAR receptors (Killer cell Activatory Receptor), counterparts of non-inhibiting KIR receptors (Keller cell Inhibitory Receptors) of the immunoglobulin or lectin type. The invention concerns in particular, novel KARAP (KAR-Associated Proteins) polypeptides and their biological applications. A KARAP polypeptide is naturally associated with a KAR receptor, and in the absence of such a KARAP, said KAR receptor is naturally incapable of transducing an activating signal that can be detected. The application also concerns methods for obtaining or identifying such KARAP polypeptides.

14 Claims, 26 Drawing Sheets

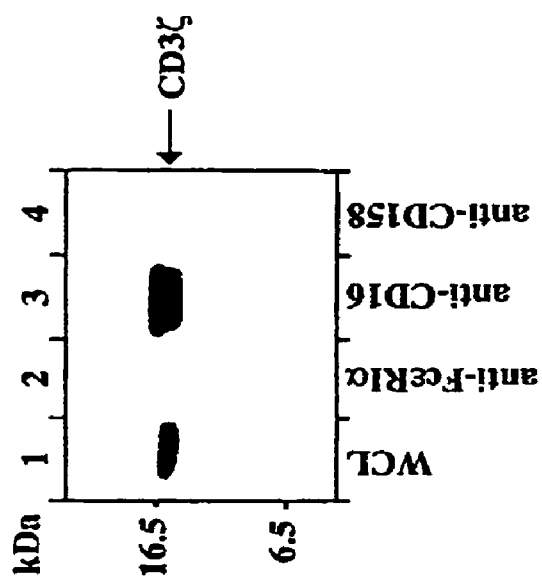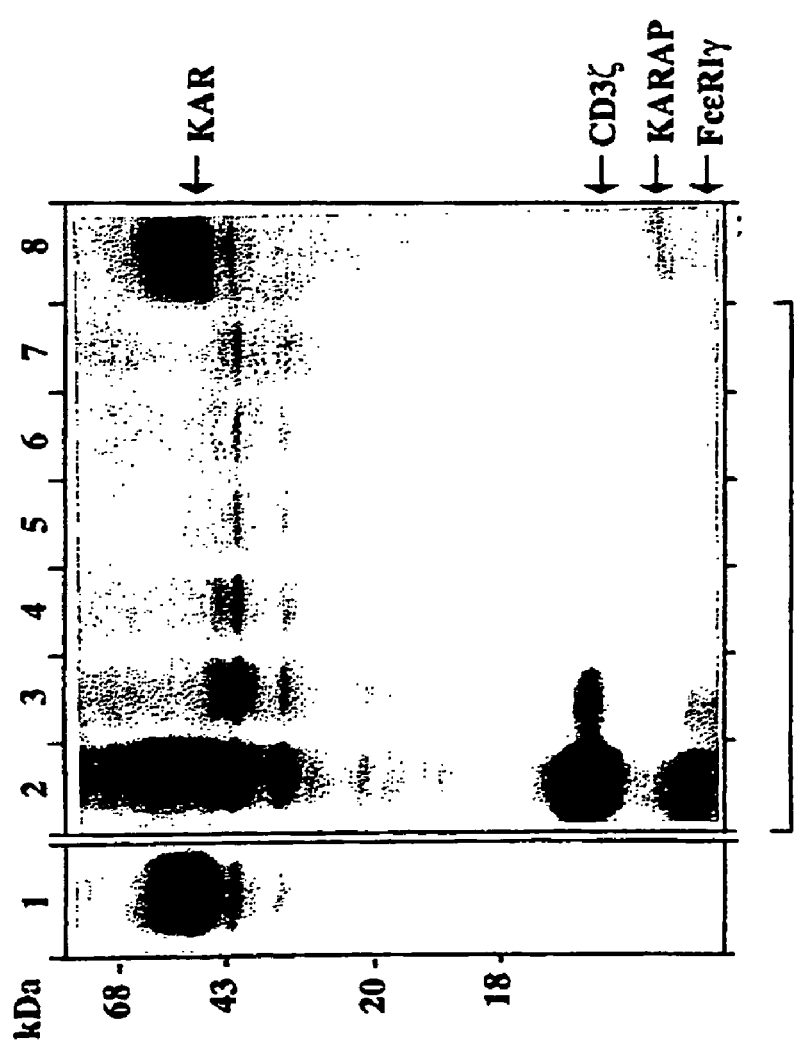

anti-CD158 IP

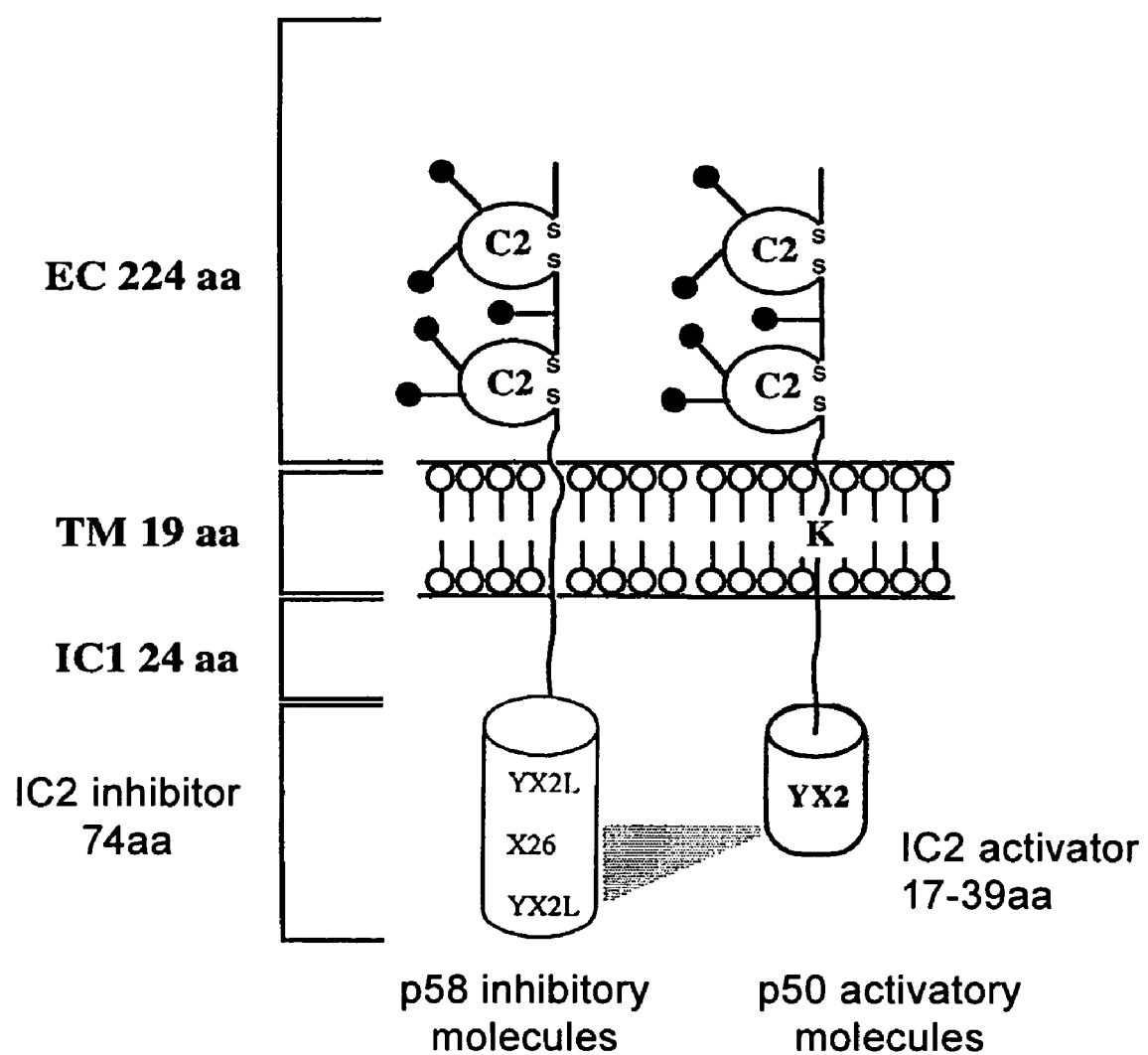

Fig. 7

Figure 1A:
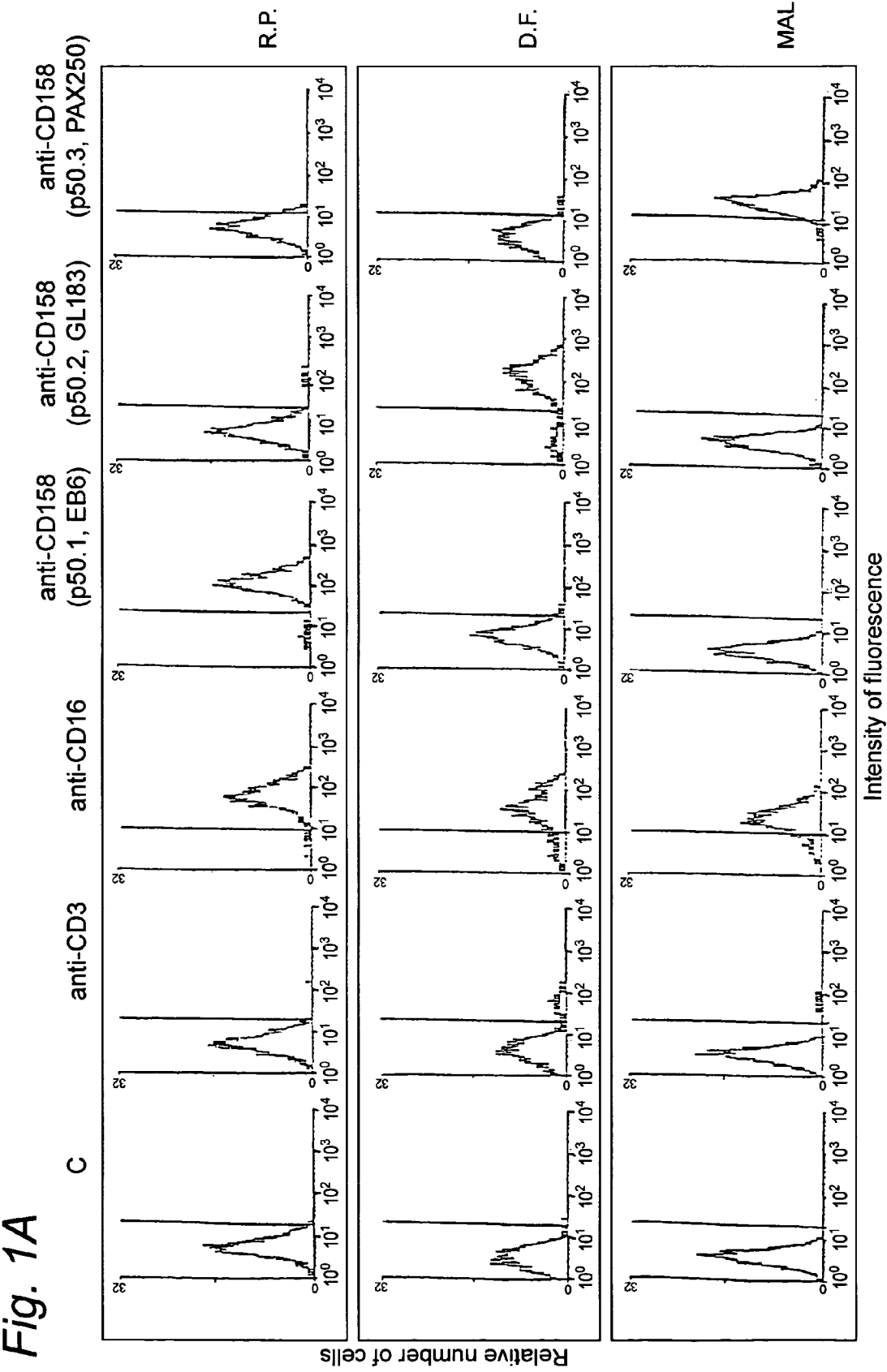

```
  1 ggtcacacca ggtcccacca gccoctggac tgtggtgtcc agtgcatatc tggccaccat
 61 ggggctctgg agcctcctgg tgccttctgt tccttcctgt cctcctgact gtgggaggat
121 taagtcccgt acaggcccag agtgacactt tcccaagatg cgactgttct tccgtgagcc
181 ctggtgtact gtctgggatt gttctgggtg acttggtgtt gactctgctg attgccctgg
241 ctgtgtactc tctgggccgc ctggtctccc gaggtcaagg gacagcggaa gggacccgga
301 aacaacacat tgctgagact gagtcgcctt atcaggagct tcagggtcag agacatgaag
361 tatacagtga cctcaacaca cagaggcaat attacagatg agcccactct atgcccatca
421 gcggcctgat gcccggatcc ggtcattcca gatgcctact caacaagccc tctctgagat
481 caggactccc gttggaatac agatccacag ggtacct
```

Fig. 8

```
1/1                                                                              31/11
cag agt gac act ttc cca aga tgc gac tgt tct tcc gtg agc cct ggt gta ctg tct ggg
 Q   S   D   T   F   P   R   C   D   C   S   S   V   S   P   G   V   L   S   G 61/21                                                                            91/31
att gtt ctg ggt gac ttg gtg ttg act ctg ctt att gcc ctg gct gtg tac tct ctg ggc
 I   V   L   G   D   L   V   L   T   L   L   I   A   L   A   V   Y   S   L   G 121/41                                                                           151/51
cgc ctg gtc tcc cga ggt caa ggg aca gcg gaa ggg acc cgg aaa caa cac att gct gag
 R   L   V   S   R   G   Q   G   T   A   E   G   T   R   K   Q   H   I   A   E 191/61                                                                           211/71
act gag tcg cct tat cag gag ctt cag ggt cag aga cat gaa gta tac agt gac ctc aac
 T   E   S   P   Y   Q   E   L   Q   G   Q   R   H   E   V   Y   S   D   L   N 241/81
aca cag agg caa tat tac aga
 T   Q   R   Q   Y   Y   R
```

Fig. 9

ITAM polypeptides

| | |
|---|---|
| CD3ζ₁ | YneLnlgrree-YdvL |
| CD3ζ₂ | YneLqkdkmaeaYseI |
| CD3ζ₃ | YqgLstatkdt-YdaL |
| CD3γ | YqpLkdreddq-YshL |
| CD3δ | YqpLrdrddaq-YshL |
| CD3ε | YepIrkgqrdl-YsgL |
| Igα (CD79a) | YedIsrglqgt-YqdV |
| Igβ (CD79b) | YegLdidqtat-YedI |
| FcεRIγ | YtgLdtrnqet-YetL |
| FcεRIβ | YeeLniysat--YseL |
| KARAP | YqeLqgqrhev-YsdL |
| Consensus | Y--L--------Y--L |
| | I           I |

Fig. 10A

SEQ ID n°6

```
         10         20         30         40         50
1234567890 1234567890 1234567890 1234567890 1234567890
TCACACCAGG TCCCACCAGC CCCTGGACTG TGGTGTCCAG TGCATATCTG   50
GCCACCATGG GGCTCTGGAG CCTCCTGGTG CCTTCTGTTC CTTCCTGTCC  100
TCCTGACTGT GGGAGGATTA AGTCCCGTAC AGGCCCAGAG TGACACTTTC  150
CCAAGATGCG ACTGTTCTTC CGTGAGCCCT GGTGTACTGT CTGGGATTGT  200
TCTGGGTGAC TTGGTGTTGA CTCTGCTGAT TGCCCTGGCT GTGTACTCTC  250
TGGGCCGCCT GGTCTCCCGA GGTCAAGGGA CAGCGGAAGG GACCCGGAAA  300
CAACACATTG CTGAGACTGA GTCGCCTTAT CAGGAGCTTC AGGGTCAGAG  350
ACATGAAGTA TACAGTGACC TCAACACACA GAGGCAATAT TACAGATGAG  400
CCCACTCTAT GCCCATCAGC GGCCTGATGC CCGGATCCGG TCATTCCAGA  450
TGCCTACTCA ACAAGCCCTC TCTGAGATCA GGACTCCCGT TGGAATACAG  500
ATCCACAGGG TACCT                                        515
```

Fig. 10B

```
         10         20         30         40         50
1234567890 1234567890 1234567890 1234567890 1234567890
SHQVPPAPGL WCFVHIWPFW GSGASWCLLF LPVLLTVGGL SPVQAQSDTF   50
PRCDCSSVSP GVLSGIVLGD LVLTLLIALA VYSLGRLVSR GQGTAEGTRK  100
QHIAETESPY QELQGQRHEV YSDLNTQRQY YRXAHSMPIS GLMPGSGHSR  150
CLLNKPSLRS GLPLEYRSTG Y                                 171
```

SEQ ID n°11

Fig. 11A

SEQ ID n°7

```
         10         20         30         40         50
1234567890 1234567890 1234567890 1234567890 1234567890
GTGCATATCT GGCCACCATG GGGGCTCTGG AGCCTCCATG GTGCCTTCTG    50
TTCCTTCCTG TCCTCCTGAC TGTGGGAGGA TTAAGTCCCG TACAGGCCCA   100
GAGTGACACT TTCCCAAGAT GCGACTGTTC TTCCGTGAGC CCTGGTGTAC   150
TGGCTGGGAT TGTTCTGGGT GACTTGGTGT TGAGTCTGCT GATTGCCCTG   200
GGTGTGTACT CTCTCGGCCG CCTGGTCTCC CGAGGTCAAG GGACAGCCGA   250
AGGGACCCGG AAACAACACA TTGCTGAGAC TGAGTCCCT TATCAGGAGC   300
TTCAGGGTCA GAGACCAGAA GTATACAGTG ACCTCAACAC ACAGAGGCAA   350
TATTACAGAT GAGCCCACTC T                                  371
```

Fig. 11B

```
         10         20         30         40         50
1234567890 1234567890 1234567890 1234567890 1234567890
AYLATMGALE PPWCLLFLPV LLTVGGLSPV QAQSDTFPRC DCSSVSFGVL    50
AGIVLGDLVL TLLIALAVYS LGRLVSRGQG TAEGTRKQHI AETESPYQEL   100
QGQRPEVYSD LNTQRQYYRX AFS                                123
```

SEQ ID n°12

Fig. 12A

SEQ ID n°8

```
         10         20         30         40         50
1234567890 1234567890 1234567890 1234567890 1234567890
GCCTTCTGTT CTTCCTGTC CTCCTGACTG TGGGAGGATT AAGTCCCGTA    50
CAGGCCCAGA GTCACACTTT CCCAAGATGC CGCTGTTCTT CCGTGAGCCC  100
TGGTGTACTG GCTGGGATTG TTCTGGGTGA CTTGGTGTTG ACTCTGCTGA  150
TTGCCCTGGC TGTGTACTCT CTGGGCCGCC TGGTCTCCCG AGGTCAAGGG  200
ACAGCCGAAG CGACCCGGAA ACAACACATT GCTGAGACTG AGTCGCCTTA  250
TCAGGAGCTT CAGGGTCAGA GACATGAAGT ATACAGTGAC CTCAACACAC  300
AGAGGCAATA TTACGAGTGA GCCCACTCTA TGCCCATCAG CGGCCTGATG  350
CCCGGATCCG GTCATTCCAG ATGCCT                           376
```

Fig. 12B

```
         10         20         30         40         50
1234567890 1234567890 1234567890 1234567890 1234567890
LLFLPVLLTV GGLSFVQAQS DTFPRCGCSS VSPGVLAGIV LGDLVLTLLI    50
ALAVYSLGRL VSRGQGTAEG TRKQHIAETE SPYQELQGQR HEVYSDLNTQ  100
RQYYEXAHSM PISGLMPGSG HSRC                             124
```

SEQ ID n°13

Fig. 13A

SEQ ID n°9

|  | 10 | 20 | 30 | 40 | 50 | |
|---|---|---|---|---|---|---|
|  | 1234567890 | 1234567890 | 1234567890 | 1234567890 | 1234567890 | |
|  | CCAGCCCCTG | GACTGTGGTG | TCCAGTGCAT | ATCTGGCCAC | CATGGGGCT | 50 |
|  | CTGGAGCCTC | CTGGTGCCTT | CTGTTCCTTC | CTGTCCTCCT | GACTGTGGGA | 100 |
|  | GGATTAAGTC | CGGTACAGGC | CCAGAGTGAC | ACTTTCCCAA | GATGCGACTG | 150 |
|  | TTCTTCCGTG | AGCCCTGGTG | TACTGGCTGG | GATTGTTCTG | GGTGACTTGG | 200 |
|  | TGTTGACTCT | GCTGATTGCC | CTGGCTGTGT | ACTCTCTGGG | CCGCCTGGTC | 250 |
|  | TCCCGAGGTC | AAGGGACAGC | GGAAGGGACC | CGGAAACAAC | ACATTGCTGA | 300 |
|  | GACTGAGTCG | CCTTATCAGG | AGCTTCAGGG | TCAGAGACCA | GAAGTATACA | 350 |
|  | GTGACCTCAA | CACACAGAGG | CAATATTACA | GATGAGCCAC | TCTATGCCCA | 400 |
|  | TC |  |  |  |  | 402 |

Fig. 13B

|  | 10 | 20 | 30 | 40 | 50 | |
|---|---|---|---|---|---|---|
|  | 1234567890 | 1234567890 | 1234567890 | 1234567890 | 1234567890 | |
|  | QPLDCGVQCI | SGHHGGSGAS | WCLLFLPVLL | TVGGLSPVQA | QSDTFPRCDC | 50 |
|  | SSVSPGVLAG | IVLGILVLTL | LIALAVYSLG | RLVSRGQGTA | EGTRKQHIAE | 100 |
|  | TESPYQELQG | QRPEVYSDLN | TQRQYYRXAT | LCP |  | 133 |

SEQ ID n°14

Fig. 14A

SEQ ID n°10

```
          10         20         30         40         50
  1234567890 1234567890 1234567890 1234567890 1234567890
  GTTCCTTCCT GTCCTCCTGA CTGTCGGAGG ATTAAGTCCC GTACAGCCCC    50
  AGAGTGACAC TTTCCCAAGA TGCGACTGTT CTTCCGTGAG CCCTGGTGTA   100
  CTGGCTGGGA TGTTCTGGG TGACTTGGTG TTGACTCTCC TGATTGCCCT    150
  CGCTGTGTAC TCTCTGGCC GCCTGGTCTC CGAGGTCAA GGGACAGCGG    200
  AAGGGACCCG GAAACAACAC ATTGCTGAGA CTGAGTCGCC TTATCAGGAG   250
  CTTCAGGGTC AGAGACCTGA AGTATACAGT GACCTCAACA CACAGAGCCG   300
  ATATTACAGA TGAGCCCACT CTATGCCCAT CAGCGGCCTG ATGCCCGGAT   350
  CCGGTCATTC CAGATGCCTA CTCAACAAGC CCTTCTGTGG GATCAGGACT   400
  CCCGTTGGAA TACAGATCCA CAGGGTACCT CCCTGAGATA TCTGACATTG   450
  TACCATTTCT GTCCCAAAT AGAAGACGGA CA                      482
```

Fig. 14B

```
          10         20         30         40         50
  1234567890 1234567890 1234567890 1234567890 1234567890
  FLFVLLTVGG LSFVQACSDT FFRCDCSSVS PGVLAGIVLG DLVLTLLIAL    50
  AVYSLGRLVS FQQGTAEGTR KQHIAETESP YQELQGQRPE VYSDLNTQRR   100
  YYRXAHSMPI SGLMPGSGHS RCLLNKPFCG IRTFVGIQIH RVPPXDDXHC   150
  TISVFXXKID                                               160
```

SEQ ID n°15

Fig. 15

```
SEQ ID n°9  AA098506   ---------- -----..... .......... .......... ..........  35
SEQ ID n°6  AA242315   .......... .......... .......... .......... ..........  50
SEQ ID n°8  W88159     ---------- ---------- ---------- ---------- ----------
SEQ ID n°7  AA734769   ---------- ---------- ---------- ---------- ---------.  11
SEQ ID n°10 W41142     ---------- ---------- ---------- ---------- ----------
SEQ ID n°16 Consensus  TCACACCAGG TCCCACCAGC CCCTGGACTG TGGTGTCCAG TGCATATCTG  50

AA098506   .......... .......... ........-. .......... ..........  84
            AA242315   .......... ..-....... ......-... .......... ..........  98
            W88159     ---------- ---------- ---------- -......... ..........  19
            AA734769   .......... .......... .......... .......... ..........  61
            W41142     ---------- ---------- ---------- --------.. ..........  12
            Consensus  GCCACCATGG GGGCTCTGGA GCCTCCATGG TGCCTTCTGT TCCTTCCTGT 100

AA098506   .......... .......... .......... .......... .......... 134
            AA242315   .......... .......... .......... .......... .......... 148
            W88159     .......... .......... .......... .......... ..........  69
            AA734769   .......... .......... .......... .......... .......... 111
            W41142     .......... .......... .......... .......... ..........  62
            Consensus  CCTCCTGACT GTGGGAGGAT TAAGTCCCGT ACAGGCCCAG AGTGACACTT 150

AA098506   .......... ..A....... .......... .......... .G........ 184
            AA242315   .......... ..A....... .......... .......... .T........ 198
            W88159     .......... ..G....... .......... .......... .G........ 119
            AA734769   .......... ..A....... .......... .......... .G........ 161
            W41142     .......... ..A....... .......... .......... .G........ 112
            Consensus  TCCCAAGATG CGRCTGTTCT TCCGTGAGCC CTGGTGTACT GKCTGGGATT 200

AA098506   .......... .......... .......... .......... .......... 234
            AA242315   .......... .......... .......... .......... .......... 248
            W88159     .......... .......... .......... .......... .......... 169
            AA734769   .......... .......... .......... .......... .......... 211
            W41142     .......... .......... .......... .......... .......... 162
            Consensus  GTTCTGGGTG ACTTGGTGTT GACTCTGCTG ATTGCCCTGG CTGTGTACTC 250

AA098506   ...G...... .......... .......... .......... .......... 284
            AA242315   ...G...... .......... .......... .......... .......... 298
            W88159     ...G...... .......... .......... .......... .......... 219
            AA734769   ...C...... .......... .......... .......... .......... 261
            W41142     ...G...... .......... .......... .......... .......... 212
            Consensus  TCTSGGCCGC CTGGTCTCCC GAGGTCAAGG GACAGCGGAA GGGACCCGGA 300

AA098506   .......... .......... .......... .......... .......... 334
            AA242315   .......... .......... .......... .......... .......... 348
            W88159     .......... .......... .......... .......... .......... 269
            AA734769   .......... .......... .......... .......... .......... 311
            W41142     .......... .......... .......... .......... .......... 262
            Consensus  AACAACACAT TGCTGAGACT GAGTCGCCTT ATCAGGAGCT TCAGGGTCAG 350

AA098506   .....CA... .......... .......... .......A.. .......... 384
            AA242315   .....AT... .......... .......... .......A.. .......... 398
            W88159     .....AT... .......... .......... ........A. .......... 319
            AA734769   .....CA... .......... .......... .......A.. .......... 361
            W41142     .....CT... .......... .......... .......G.. .......... 312
            Consensus  AGACMWGAAG TATACAGTGA CCTCAACACA CAGAGGCRAT ATTACAGATG 400
```

Fig. 15 (contd.)

```
AA098506     ....-.....  ..........-  ----------  ----------  ----------   402
AA242315     ..........  ..........  ..........  ..........  ..........   448
W88159       ..........  ..........  ..........  ..........  ..........   369
AA734769     ..........  ----------  ----------  ----------  ----------   371
W41142       ..........  ..........  ..........  ..........  ..........   362
Consensus    AGCCCACTCT  ATGCCCATCA  GCGGCCTGAT  GCCCGGATCC  GGTCATTCCA    450

AA098506     ----------  ----------  ----------  ----------  ----------   402
AA242315     ..........  ..........  .-..C..A..  ..........  ..........   497
W88159       .......---  ----------  ----------  ----------  ----------   376
AA734769     ----------  ----------  ----------  ----------  ----------   371
W41142       ..........  ..........  ....G..G..  ..........  ..........   412
Consensus    GATGCCTACT  CAACAAGCCC  TTCTSTGRGA  TCAGGACTCC  CGTTGGAATA    500

AA098506     ----------  ----------  ----------  ----------  ----------   402
AA242315     ..........  ......---  ----------  ----------  ----------   515
W88159       ----------  ----------  ----------  ----------  ----------   376
AA734769     ----------  ----------  ----------  ----------  ----------   371
W41142       ..........  ..........  ..........  ..........  ..........   462
Consensus    CAGATCCACA  GGGTACCTCC  CTGAGATATC  TGACATTGTA  CCATTTCTGT    550

AA098506     ----------  ----------                                         402
AA242315     ----------  ----------                                         515
W88159       ----------  ----------                                         376
AA734769     ----------  ----------                                         371
W41142       ..........  ..........                                         482
Consensus    CCCCAAATAG  AAGACGGACA                                         570
```

Fig. 16

|  | | | | | |
|---|---|---|---|---|---|
| SEQ ID n°11 AA242315 protein | SHQVPPAPGL | WCPVHIWPPW | GSGAS..... | .......... | .......... | 50 |
| SEQ ID n°13 W88159 protein | ---------- | ---------- | ---------- | ---------- | ---------- | 23 |
| SEQ ID n°15 W41142 protein | ---------- | ---------- | ---------- | ---------- | ---------- | 21 |
| SEQ ID n°14 AA098506 protein | QPLDCGVQCI | SGHHG..... | GSGAS..... | .......... | .......... | 45 |
| SEQ ID n°12 AA734769 protein | AYL....... | .ATMG..... | ALEPP..... | .......... | .......... | 37 |

| SEQ ID n°17 Consensus | .......... | .......... | ....WCLLF | LPVLLTVGGL | SPVQAQSD | 50 |

| AA242315 protein | .......... | .......... | .......... | .......... | .......... | 150 |
| W88159 protein   | ......S... | .........S | .......... | .......... | .......... | 73 |
| W41142 protein   | .......... | .......... | .......... | .......... | .......... | 71 |
| AA098506 protein | .......... | .......... | .......... | .......... | .......... | 95 |
| AA734769 protein | .......... | .......... | ......R... | .......... | .......... | 87 |

| Consensus | PRCDCSSVSP | GVLAGIVLGD | LVLTLLIALA | VYSLGRLVSR | GQGTAEGT | 100 |

| AA242315 protein | .......... | .......H.. | .......... | .......X.. | .......... | 150 |
| W88159 protein   | .......... | .......H.. | .......... | .......X.. | .......... | 123 |
| W41142 protein   | .......... | .......... | .......... | .......X.. | .......... | 121 |
| AA098506 protein | .......... | .......... | .......R.. | .......X.TL | ---....... | 131 |
| AA734769 protein | .......... | .......... | .......... | .......X.. | .......... | 123 |

| Consensus | QHIAETESPY | QELQGQRPEV | YSDLNTQRQY | YR.AHSMPIS | GLMPGSGH | 150 |

| AA242315 protein | .LLNKP..SL | RSGLPLEY.. | .......... | .......... | ..RSTGY | 171 |
| W88159 protein   | .LLNKPFCGI | RTPVGIQIHR | VPPXDIXHCT | ISVPKXKID | .......... | 124 |
| W41142 protein   | .......... | .......... | .......... | .......... | .......... | 150 |
| AA098506 protein | ---....... | .......... | ......CP.. | .......... | .......... | 133 |
| AA734769 protein | ---------- | ---------- | ---------- | ---------- | ---------- | 123 |

| Consensus | C--------- | ---------- | ---------- | ---------- | ---------- | 199 |

Fig. 17

SEQ ID n°18

```
           10         20         30         40         50
  1234567890 1234567890 1234567890 1234567890 1234567890
  ACACCAGGTC CCACCAGCCC CTGGACTGTG GTGTCCAGTG CATATCTGCC    50
  CACCATGGGG GCTCTGGAGC CCTCCTGGTG CCTTCTGTTC CTTCCTGTCC   100
  TCCTGACTGT GGAGGTGAGT CGGGCGGCTT CTGTGGATGC CTCCTGTGTC   150
  CTCAGCTCAT GTTGGGGCCA GGACTAGGCA GAGAGCAGGA AGGGACAGCA   200
  CAGACAAGGG GAAGGCTGGG CAGAAGAAGG TTCCTCTAGA GCCTGTGGGT   250
  TTCACCCTGA GCTAGAGGCC CTGAGATTTG GAACCTGGTA GTATCAGTAG   300
  GGGGACATT  GAAGCTCACA GATATACCTA CCACATGTTG GTCAGTACCG   350
  GCGGCTGGGT GCTGTGAGAC CAGCTCTTTC CAACCTTCTT CACCTTCTAC   400
  ATCCACTGTC TGTGCCTCAA TTTACATCTT TCTTTTGAAT ATAGAATCAC   450
  ATATAGCCCA GGCTAGCTTC AAATTTGCTA CGTAATTGAG GATAACCTCA   500
  ACCTTTCTAT TCTCTGTCTC CACCTCTCT  AGTTTACCTG TTCTTTTCTC   550
  CTTAGGATTA AGTCCGTAC  AGCCCAGAG  TGGTAAGCCA TAATACCCCC   600
  GATCTTTCTC TCTTCCTCTC AAAGACCTCC TCAGGCCACC CCTTCTCCTT   650
  CTAGCCCTCT TTGTGCTAAC ACCAAGCCCT GATTGTTAAC CTGTGTCCCC   700
  CTCTTCATCC TCCTGAGACA CTTTCCCAAG ATGCGACTGT TCTTCCGTGA   750
  GCCCTGGTGT ACTGGCTGGG ATTGTTCTGG GTCACTTGGT GTTGACTCTG   800
  CTGATTGCCC TGGCTGTGTA CTCTCTGGCC CGCCTGGTCT CCCGAGGTCA   850
  AGAGAGTAAG AAGGTAAATA AATCTTTAAA AAAAATTGTC CCAGTCCCCA   900
  GCTTAGTCCT TCTTCACACC ATATGTCACT CTCTATCCCT CTCTAGGGAC   950
  CCGAAACAA  CACATTGCTG AGACTGAGTC GCCTTATCAG GTAAGAACGC  1000
  CAAATTCTTC TCCACCCTTG CTCCTGCCCC GTCCTGGCTA TCCCCTCCC   1050
  CAGTACAGAC ACACAGACAA ACACACACAC ACAAATACAC AGAGACATAT  1100
  ATAAACACAC TCACATAAAT AAACACACAC ACATACCTAC ACACACACAC  1150
  ACACATACCT ACACACACAC ACACACATAC CTACACACAC ACACACACAC  1200
  ACACACACAC ACTACCCTTC CCAGAACCTT AAGGTCCCTT CCTCAGGAGC  1250
  TCCCCCAATC CTGAAGGCAA AGGACTAACT GTCAAACATA TTCGGTGGTC  1300
  AACCATGACC TTTAAGCTCA GCTTCTAATG AGTCTCTTGT CAAGATTCTA  1350
  TTCCTCTGTC TCTCTCTCTC TCTCTCTCTC TCTCTCTCTC TCTCTCTCTC  1400
  TCTCTCTCTC TCTGCGTGTG TGTGTGTGTG TGTGTGTGTG TGTGTAGGCA  1450
  GGTTATAAGA GGACATCAAA TCCTATCTTT ACCTTATTTT TAAAATGGCA  1500
  CTGATTTTGC TCTGTATTTA CATGTGTGTG TGGAGCAGGT GTGCATATGC  1550
  ACTGGCAGCC ATGTGGGGT  CAGAAGACAA CCCGTGGGGG CTGGTTCTCT  1600
  CCTTCCACCT TGTGGATCTC TGAACTCTAA ATTCTAGTTG TCAAGCTTGG  1650
  CAGCAAGTGC TTTACCCACT GAACCATCTC ACCAGCCCCA AGCCTCCTTC  1700
  CTAACCTTTG GGCTCTGGGT GAGGCTATGT CTCTAGGAA  ACACACACCA  1750
  GGCTGGTCTC TGGTACATGC TCTCAGAGAC TCTGCCCCTG GGAGGCACAG  1800
  ACCCCTGCTC TGTGACCCAA TTTCTGGAAG TCTACCTCCC TCCCTGTAGC  1850
  CAGTTTTGCC CATTCGACTG ACTCCTTGCT GGAGGAACTT TTTCTCTGAA  1900
  AAGTGTTAGA ATCTCTTGAT TCTTGTTTTG AGTTTGGTGT GGGGAAGTAG  1950
  TGCCGTGTGT CTTTAATCCC AGCGCTCTGG TGGCAGAGGT AGGCAGATCT  2000
  CTGTGAATTT GACGGCTGGCC TGGTCTACAG TGTGAGTTCC TGGACAGGCA  2050
```

SEQ ID n°18 (contd.)

Fig. 17 (contd.)

```
         10         20         30         40         50
1234567890 1234567890 1234567890 1234567890 1234567890
GGGCTACCCA AAGAAACCCT GTCTACAAGC AAACAAACAA ACAAAAACAA  2100
AACAAAACAA AAAAGAATCT CAATATTGGC CATCTGATGT CCAGAAGACC  2150
CCGGGCTGTC TAGTTTCTGA GAGCCAGGAA ACTTTAGGGC AAATGTCAGC  2200
CTGATTTTTT TATCCTTCGG TATCTTGGTT GAGCCTACA TGGATCAACA   2250
CAGCACTCCA ATTGGAGAAG CTTATTTGAA GCAACTTAAC AAAATCATTT  2300
GGGGTGACAT TATGAAGAGA TTGAAGTGAA CCAATATAAT GGTGGGACAG  2350
GAAAGAAACT GAAGATGGGG AAACTAAAAC ATTGCCAAGA CTCAAAGGGT  2400
GACCAGGTTG AAGATCTGTG GGCTTGGTGC TCCAGGCATC GGGGTGGGGG  2450
GCTGCACATG TAAGAACCCT GGGGTTGGTG CCTAATGTGC AGCCAGAAAG  2500
GCCAGGAGAA TGCTGAGTGC ATTGAATAA AATCTTGACC TTTTCATGAT   2550
TTTAAGTTTG AAAAACCTGC CAGAGACCTT GAGGTCATT AGAGGCTAG    2600
ATTTGTTTTT ATTTCCTGGG CCCCCTCCAA TGATGCCCTT TTTTTTTTTT  2650
TTTAAGGAGC TTCAGGGTCA GAGACCAGAA GTATACAGTG ACCTCAACAC  2700
ACAGAGGCAA TATTACAGAT GAGCCCACTC TATGCCCATC AGCGGCCCTGA 2750
TGCCCGGATC CGGTCATTCC AGATGCCTAC TCAACAAGCC CTCTCTGAGA  2800
TCAGGACTCC CGTTGGAATA CAGATCCACA GGGTACCT              2838
```

Fig. 18

| 3' Intron sequence (donor site) | Exon Sequence | 5' Intron sequence (acceptor site) |
|---|---|---|
| | MetGly           alGluG<br>ATGGGG..-Exon 1-..TGGAGG | GAGGTGA.... |
| ....TCCTTAG | lyLeuS            lnSerA<br>GATTAA..-Exon 2-..AGAGTG | GTAAGCC.... |
| ....TCCTGAG | spThrP            lnGluA<br>ACACTT..-Exon 3-..AAGAGA | GTAAGAA.... |
| ....TCTCTAG | rgThrA            TyrGln<br>GGACCC..-Exon 4-..TATCAG | GTAAGAA.... |
| ....TTTTAAG | | |

Fig. 19

```
                    10         20         30         40         50
              1234567890 1234567890 1234567890 1234567890 1234567890
SEQ ID n°27   ATGGGGGCTC TGGAGCCCTC CTGGTGCCTT CTGTTCCTTC CTGTCCTCCT     50
SEQ ID n°28    M  G  A  L  E  P  S  W  C  L  L  F  L  P  V  L  L

GACTGTGGAG GGATTAAGTC CCGTACAGGC CCAGAGTGAC ACTTTCCCAA    100
               T  V  E  G  L  S  P  V  Q  A  Q  S  D  T  F  P  R

GATGCGACTG TTCTTCCGTG AGCCCTGGTG TACTGGCTGG GATTGTTCTG    150
               C  D  C  S  S  V  S  P  G  V  L  A  G  I  V  L

GGTGACTTGG TGTTGACTCT GCTGATTGCC CTGGCTGTGT ACTCTCTGGG    200
               G  D  L  V  L  T  L  L  I  A  L  A  V  Y  S  L  G

CCGCCTGGTC TCCCGAGGTC AAGAGAGGAC CCGGAAACAA CACAATGCTG    250
               R  L  V  S  R  G  Q  E  R  T  R  K  Q  H  I  A  E

AGACTGAGTC GCCTTATCAG GAGCTTCAGG GTCAGAGACA TGAAGTATAC    300
               T  E  S  P  Y  Q  E  L  Q  G  Q  R  H  E  V  Y

AGTGACCTCA ACACACAGAG GCAATATTAC AGATGAGCCC ACTCTATGCC    350
               S  D  L  N  T  Q  R  Q  Y  Y  R  .  A  H  S  M  P

CATCAGCGGC CTGATGCCCG GATCCGGTCA TTCCAGATGC CTACTCAACA    400
               I  S  G  L  M  P  G  S  G  H  S  R  C  L  L  N  K

AGCCCTCTCT GAGATCAGGA CTCCCGTTGG AATACAGATC CACAGGGTAC    450
               P  S  L  R  S  G  L  P  L  E  Y  R  S  T  G  Y

CT                                                        452
```

Fig. 21

SEQ ID n°31

```
         10         20         30         40         50
 1234567890 1234567890 1234567890 1234567890 1234567890
 GGCTTCGTTT TCTGTTCTGC GCCGTTACAG ATCCAAGCTC CTCGAGGGCT     50

TCATGGGGGG ACTTGAACCC TGCAGCAGGC TCCTGCTCCT GCCTCTCCTG    100
 ───
 Codon
 Initiation
 CTGGCTGTAA GTGGTCTCCG TCCTGTCCAG GCCCAGGCCC AGAGCCATTG    150

CAGTTGCTCT ACGGTGAGCC CGGGCGTGCT GGCAGCGATC GTCATCGGAG    200

ACCTGGTGCT GACAGTGCTC ATTGCCCTGG CCGTGTACTT CCTGGGCCGG    250

CTGGTCCCTC GGGGCCGAGG GGCTGCGGAG GCAGCGACCC GGAAACAGCG    300

TATCACTGAG ACCGAGTCGC CTTATCAGGA GCTCCAGGGT CAGAGGTCGG    350

ATGTCTACAG CGACCTCAAC ACACAGAGGC CGTATTACAA ATGAGCCCGA    400
                                              Stop

ATCATGACAG TCACCACAAT GATACCTGGA T                        431
```

Release of serotonin induced by the p50/KARAP complex reconstituted in RBL-2H3 cells

SEQUENCE LISTING

```
<160> NUMBER OF SEQ ID NOS: 44

<210> SEQ ID NO 1
<211> LENGTH: 517
<212> TYPE: DNA
<213> ORGANISM: Mus musculus
<220> FEATURE:
<221> NAME/KEY: CDS
<222> LOCATION: (138)..(398)

<400> SEQUENCE: 1
ggtcacacca ggtcccacca gcccctggac tgtggtgtcc agtgcatatc tggccaccat      60
ggggctctgg agcctcctgg tgccttctgt tccttcctgt cctcctgact gtgggaggat     120
taagtcccgt acaggcc cag agt gac act ttc cca aga tgc gac tgt tct        170
                    Gln Ser Asp Thr Phe Pro Arg Cys Asp Cys Ser
                     1               5                      10 tcc gtg agc cct ggt gta ctg tct ggg att gtt ctg ggt gac ttg gtg       218
Ser Val Ser Pro Gly Val Leu Ser Gly Ile Val Leu Gly Asp Leu Val
                 15                  20                  25 ttg act ctg ctg att gcc ctg gct gtg tac tct ctg ggc cgc ctg gtc       266
Leu Thr Leu Leu Ile Ala Leu Ala Val Tyr Ser Leu Gly Arg Leu Val
         30                  35                  40 tcc cga ggt caa ggg aca gcg gaa ggg acc cgg aaa caa cac att gct       314
Ser Arg Gly Gln Gly Thr Ala Glu Gly Thr Arg Lys Gln His Ile Ala
 45                  50                  55 gag act gag tcg cct tat cag gag ctt cag ggt cag aga cat gaa gta       362
Glu Thr Glu Ser Pro Tyr Gln Glu Leu Gln Gly Gln Arg His Glu Val
         60                  65                  70                  75 tac agt gac ctc aac aca cag agg caa tat tac aga tgagcccact            408
Tyr Ser Asp Leu Asn Thr Gln Arg Gln Tyr Tyr Arg
                 80                  85 ctatgcccat cagcggcctg atgcccggat ccggtcattc cagatgccta ctcaacaagc    468
cctctctgag atcaggactc ccgttggaat acagatccac agggtacct               517

<210> SEQ ID NO 2
<211> LENGTH: 87
<212> TYPE: PRT
<213> ORGANISM: Mus musculus
```

<400> SEQUENCE: 2

Gln Ser Asp Thr Phe Pro Arg Cys Asp Cys Ser Ser Val Ser Pro Gly
 1               5                   10                  15

Val Leu Ser Gly Ile Val Leu Gly Asp Leu Val Leu Thr Leu Leu Ile
             20                  25                  30

Ala Leu Ala Val Tyr Ser Leu Gly Arg Leu Val Ser Arg Gly Gln Gly
         35                  40                  45

Thr Ala Glu Gly Thr Arg Lys Gln His Ile Ala Glu Thr Glu Ser Pro
     50                  55                  60

Tyr Gln Glu Leu Gln Gly Gln Arg His Glu Val Tyr Ser Asp Leu Asn
 65                  70                  75                  80

Thr Gln Arg Gln Tyr Tyr Arg
                 85

<210> SEQ ID NO 3
<211> LENGTH: 16
<212> TYPE: PRT
<213> ORGANISM: Mus musculus

<400> SEQUENCE: 3

Gln Ser Asp Thr Phe Pro Arg Cys Asp Cys Ser Ser Val Ser Pro Gly
 1               5                   10                  15

<210> SEQ ID NO 4
<211> LENGTH: 24
<212> TYPE: PRT
<213> ORGANISM: Mus musculus

<400> SEQUENCE: 4

Val Leu Ser Gly Ile Val Leu Gly Asp Leu Val Leu Thr Leu Leu Ile
 1               5                   10                  15

Ala Leu Ala Val Tyr Ser Leu Gly
             20

<210> SEQ ID NO 5
<211> LENGTH: 47
<212> TYPE: PRT
<213> ORGANISM: Mus musculus

<400> SEQUENCE: 5

Arg Leu Val Ser Arg Gly Gln Gly Thr Ala Glu Gly Thr Arg Lys Gln
 1               5                   10                  15

His Ile Ala Glu Thr Glu Ser Pro Tyr Gln Glu Leu Gln Gly Gln Arg
             20                  25                  30

His Glu Val Tyr Ser Asp Leu Asn Thr Gln Arg Gln Tyr Tyr Arg
         35                  40                  45

<210> SEQ ID NO 6
<211> LENGTH: 515
<212> TYPE: DNA
<213> ORGANISM: Mus musculus

<400> SEQUENCE: 6
tcacaccagg tcccaccagc ccctggactg tggtgtccag tgcatatctg gccaccatgg      60
ggctctggag cctcctggtg ccttctgttc cttcctgtcc tcctgactgt gggaggatta     120
agtcccgtac aggcccagag tgacactttc ccaagatgcg actgttcttc cgtgagccct     180
ggtgtactgt ctgggattgt tctgggtgac ttggtgttga ctctgctgat tgccctggct     240
gtgtactctc tgggccgcct ggtctcccga ggtcaaggga cagcggaagg gacccggaaa     300

```
caacacattg ctgagactga gtcgccttat caggagcttc agggtcagag acatgaagta    360
tacagtgacc tcaacacaca gaggcaatat tacagatgag cccactctat gcccatcagc    420
ggcctgatgc ccggatccgg tcattccaga tgcctactca acaagccctc tctgagatca    480
ggactcccgt tggaatacag atccacaggg tacct                               515

<210> SEQ ID NO 7
<211> LENGTH: 371
<212> TYPE: DNA
<213> ORGANISM: Mus musculus

<400> SEQUENCE: 7
gtgcatatct ggccaccatg ggggctctgg agcctccatg gtgccttctg ttccttcctg     60
tcctcctgac tgtgggagga ttaagtcccg tacaggccca gagtgacact ttcccaagat    120
gcgactgttc ttccgtgagc cctggtgtac tggctgggat tgttctgggt gacttggtgt    180
tgactctgct gattgccctg ctgtgtact ctctcggccg cctggtctcc cgaggtcaag     240
ggacagcgga agggacccgg aaacaacaca ttgctgagac tgagtcgcct tatcaggagc    300
ttcagggtca gagaccagaa gtatacagtg acctcaacac acagaggcaa tattacagat    360
gagcccactc t                                                         371

<210> SEQ ID NO 8
<211> LENGTH: 376
<212> TYPE: DNA
<213> ORGANISM: Mus musculus

<400> SEQUENCE: 8
gccttctgtt ccttcctgtc ctcctgactg tgggaggatt aagtcccgta caggcccaga     60
gtgacacttt cccaagatgc ggctgttctt ccgtgagccc tggtgtactg ctgggattg     120 ttctgggtga cttggtgttg actctgctga ttgccctggc tgtgtactct ctgggccgcc    180
tggtctcccg aggtcaaggg acagcggaag ggacccggaa acaacacatt gctgagactg    240
agtcgcctta tcaggagctt cagggtcaga gacatgaagt atacagtgac ctcaacacac    300
agaggcaata ttacagatga gcccactcta tgcccatcag cggcctgatg cccggatccg    360
gtcattccag atgcct                                                    376

<210> SEQ ID NO 9
<211> LENGTH: 402
<212> TYPE: DNA
<213> ORGANISM: Mus musculus

<400> SEQUENCE: 9
ccagcccctg gactgtggtg tccagtgcat atctggccac catgggggct ctggagcctc     60
ctggtgcctt ctgttccttc ctgtcctcct gactgtggga ggattaagtc cgtacaggc    120 ccagagtgac actttcccaa gatgcgactg ttcttccgtg agccctggtg tactggctgg    180
gattgttctg ggtgacttgg tgttgactct gctgattgcc ctggctgtgt actctctggg    240
ccgcctggtc tcccgaggtc aagggacagc ggaagggacc cggaaacaac acattgctga    300
gactgagtcg ccttatcagg agcttcaggg tcagagacca gaagtataca gtgacctcaa    360
cacacagagg caatattaca gatgagccac tctatgccca tc                       402

<210> SEQ ID NO 10
<211> LENGTH: 482
<212> TYPE: DNA
```

<210> SEQ ID NO 10
<211> LENGTH: 482
<212> TYPE: DNA
<213> ORGANISM: Mus musculus

<400> SEQUENCE: 10

```
gttccttcct gtcctcctga ctgtgggagg attaagtccc gtacaggccc agagtgacac      60
tttcccaaga tgcgactgtt cttccgtgag ccctggtgta ctggctggga ttgttctggg     120
tgacttggtg ttgactctgc tgattgccct ggctgtgtac tctctgggcc gcctggtctc     180
ccgaggtcaa gggacagcgg aagggacccg gaaacaacac attgctgaga ctgagtcgcc     240
ttatcaggag cttcagggtc agagacctga agtatacagt gacctcaaca cacagaggcg     300
atattacaga tgagcccact ctatgcccat cagcggcctg atgcccggat ccggtcattc     360
cagatgccta ctcaacaagc ccttctgtgg gatcaggact cccgttggaa tacagatcca     420
cagggtacct ccctgagata tctgacattg taccatttct gtccccaaat agaagacgga     480
ca                                                                     482
```

<210> SEQ ID NO 11
<211> LENGTH: 171
<212> TYPE: PRT
<213> ORGANISM: Mus musculus
<220> FEATURE:
<221> NAME/KEY: MOD_RES
<222> LOCATION: (133)
<223> OTHER INFORMATION: Any amino acid

<400> SEQUENCE: 11

```
Ser His Gln Val Pro Pro Ala Pro Gly Leu Trp Cys Pro Val His Ile
  1               5                  10                  15

Trp Pro Pro Trp Gly Ser Gly Ala Ser Trp Cys Leu Leu Phe Leu Pro
             20                  25                  30

Val Leu Leu Thr Val Gly Gly Leu Ser Pro Val Gln Ala Gln Ser Asp
         35                  40                  45

Thr Phe Pro Arg Cys Asp Cys Ser Ser Val Ser Pro Gly Val Leu Ser
     50                  55                  60

Gly Ile Val Leu Gly Asp Leu Val Leu Thr Leu Leu Ile Ala Leu Ala
 65                  70                  75                  80

Val Tyr Ser Leu Gly Arg Leu Val Ser Arg Gly Gln Gly Thr Ala Glu
                 85                  90                  95

Gly Thr Arg Lys Gln His Ile Ala Glu Thr Glu Ser Pro Tyr Gln Glu
            100                 105                 110

Leu Gln Gly Gln Arg His Glu Val Tyr Ser Asp Leu Asn Thr Gln Arg
        115                 120                 125

Gln Tyr Tyr Arg Xaa Ala His Ser Met Pro Ile Ser Gly Leu Met Pro
    130                 135                 140

Gly Ser Gly His Ser Arg Cys Leu Leu Asn Lys Pro Ser Leu Arg Ser
145                 150                 155                 160

Gly Leu Pro Leu Glu Tyr Arg Ser Thr Gly Tyr
                165                 170
```

<210> SEQ ID NO 12
<211> LENGTH: 123
<212> TYPE: PRT
<213> ORGANISM: Mus musculus
<220> FEATURE:
<221> NAME/KEY: MOD_RES
<222> LOCATION: (120)
<223> OTHER INFORMATION: Any amino acid

<400> SEQUENCE: 12

```
Ala Tyr Leu Ala Thr Met Gly Ala Leu Glu Pro Pro Trp Cys Leu Leu
 1               5                  10                  15

Phe Leu Pro Val Leu Leu Thr Val Gly Gly Leu Ser Pro Val Gln Ala
             20                  25                  30

Gln Ser Asp Thr Phe Pro Arg Cys Asp Cys Ser Ser Val Ser Pro Gly
         35                  40                  45

Val Leu Ala Gly Ile Val Leu Gly Asp Leu Val Leu Thr Leu Leu Ile
     50                  55                  60

Ala Leu Ala Val Tyr Ser Leu Gly Arg Leu Val Ser Arg Gly Gln Gly
 65                  70                  75                  80

Thr Ala Glu Gly Thr Arg Lys Gln His Ile Ala Glu Thr Glu Ser Pro
                 85                  90                  95

Tyr Gln Glu Leu Gln Gly Gln Arg Pro Glu Val Tyr Ser Asp Leu Asn
            100                 105                 110

Thr Gln Arg Gln Tyr Tyr Arg Xaa Ala His Ser
        115                 120
```

<210> SEQ ID NO 13
<211> LENGTH: 124
<212> TYPE: PRT
<213> ORGANISM: Mus musculus
<220> FEATURE:
<221> NAME/KEY: MOD_RES
<222> LOCATION: (106)
<223> OTHER INFORMATION: Any amino acid

<400> SEQUENCE: 13

```
Leu Leu Phe Leu Pro Val Leu Leu Thr Val Gly Gly Leu Ser Pro Val
 1               5                  10                  15

Gln Ala Gln Ser Asp Thr Phe Pro Arg Cys Gly Cys Ser Ser Val Ser
             20                  25                  30

Pro Gly Val Leu Ala Gly Ile Val Leu Gly Asp Leu Val Leu Thr Leu
         35                  40                  45

Leu Ile Ala Leu Ala Val Tyr Ser Leu Gly Arg Leu Val Ser Arg Gly
     50                  55                  60

Gln Gly Thr Ala Glu Gly Thr Arg Lys Gln His Ile Ala Glu Thr Glu
 65                  70                  75                  80

Ser Pro Tyr Gln Glu Leu Gln Gly Gln Arg His Glu Val Tyr Ser Asp
                 85                  90                  95

Leu Asn Thr Gln Arg Gln Tyr Tyr Arg Xaa Ala His Ser Met Pro Ile
            100                 105                 110

Ser Gly Leu Met Pro Gly Ser Gly His Ser Arg Cys
        115                 120
```

<210> SEQ ID NO 14
<211> LENGTH: 133
<212> TYPE: PRT
<213> ORGANISM: Mus musculus
<220> FEATURE:
<221> NAME/KEY: MOD_RES
<222> LOCATION: (128)
<223> OTHER INFORMATION: Any amino acid

<400> SEQUENCE: 14

```
Gln Pro Leu Asp Cys Gly Val Gln Cys Ile Ser Gly His His Gly Gly
 1               5                  10                  15

Ser Gly Ala Ser Trp Cys Leu Leu Phe Leu Pro Val Leu Leu Thr Val
             20                  25                  30

Gly Gly Leu Ser Pro Val Gln Ala Gln Ser Asp Thr Phe Pro Arg Cys
```

```
                     35                  40                  45
Asp Cys Ser Ser Val Ser Pro Gly Val Leu Ala Gly Ile Val Leu Gly
         50                  55                  60

Asp Leu Val Leu Thr Leu Leu Ile Ala Leu Ala Val Tyr Ser Leu Gly
 65                  70                  75                  80

Arg Leu Val Ser Arg Gly Gln Gly Thr Ala Glu Gly Thr Arg Lys Gln
                 85                  90                  95

His Ile Ala Glu Thr Glu Ser Pro Tyr Gln Glu Leu Gln Gly Gln Arg
            100                 105                 110

Pro Glu Val Tyr Ser Asp Leu Asn Thr Gln Arg Gln Tyr Tyr Arg Xaa
        115                 120                 125

Ala Thr Leu Cys Pro
    130
```

<210> SEQ ID NO 15
<211> LENGTH: 160
<212> TYPE: PRT
<213> ORGANISM: Mus musculus
<220> FEATURE:
<221> NAME/KEY: MOD_RES
<222> LOCATION: (104)
<223> OTHER INFORMATION: Any amino acid
<220> FEATURE:
<221> NAME/KEY: MOD_RES
<222> LOCATION: (145)
<223> OTHER INFORMATION: Any amino acid
<220> FEATURE:
<221> NAME/KEY: MOD_RES
<222> LOCATION: (148)
<223> OTHER INFORMATION: Any amino acid
<220> FEATURE:
<221> NAME/KEY: MOD_RES
<222> LOCATION: (157)

<400> SEQUENCE: 15

```
Phe Leu Pro Val Leu Leu Thr Val Gly Gly Leu Ser Pro Val Gln Ala
  1               5                  10                  15

Gln Ser Asp Thr Phe Pro Arg Cys Asp Cys Ser Ser Val Ser Pro Gly
                 20                  25                  30

Val Leu Ala Gly Ile Val Leu Gly Asp Leu Val Leu Thr Leu Leu Ile
             35                  40                  45

Ala Leu Ala Val Tyr Ser Leu Gly Arg Leu Val Ser Arg Gly Gln Gly
         50                  55                  60

Thr Ala Glu Gly Thr Arg Lys Gln His Ile Ala Glu Thr Glu Ser Pro
 65                  70                  75                  80

Tyr Gln Glu Leu Gln Gly Gln Arg Pro Glu Val Tyr Ser Asp Leu Asn
                 85                  90                  95

Thr Gln Arg Arg Tyr Tyr Arg Xaa Ala His Ser Met Pro Ile Ser Gly
            100                 105                 110

Leu Met Pro Gly Ser Gly His Ser Arg Cys Leu Leu Asn Lys Pro Phe
        115                 120                 125

Cys Gly Ile Arg Thr Pro Val Gly Ile Gln Ile His Arg Val Pro Pro
    130                 135                 140

Xaa Asp Ile Xaa His Cys Thr Ile Ser Val Pro Lys Xaa Lys Thr Asp
145                 150                 155                 160
```

<210> SEQ ID NO 16
<211> LENGTH: 570
<212> TYPE: DNA
<213> ORGANISM: Artificial Sequence
<220> FEATURE:

<223> OTHER INFORMATION: Description of Artificial Sequence: Consensus
      sequence

<400> SEQUENCE: 16

| | | | | | |
|---|---|---|---|---|---|
| tcacaccagg | tcccaccagc | ccctggactg | tggtgtccag | tgcatatctg | gccaccatgg | 60 |
| gggctctgga | gcctccatgg | tgccttctgt | tccttcctgt | cctcctgact | gtgggaggat | 120 |
| taagtcccgt | acaggcccag | agtgacactt | tcccaagatg | cgrctgttct | tccgtgagcc | 180 |
| ctggtgtact | gkctggratt | gttctgggtg | acttggtgtt | gactctgctg | attgccctgg | 240 |
| ctgtgtactc | tctsggccgc | ctggtctccc | gaggtcaagg | gacagcggaa | gggacccgga | 300 |
| aacaacacat | tgctgagact | gagtcgcctt | atcaggagct | tcagggtcag | agacmwgaag | 360 |
| tatacagtga | cctcaacaca | cagaggcrat | attacagatg | agcccactct | atgcccatca | 420 |
| gcggcctgat | gcccggatcc | ggtcattcca | gatgcctact | caacaagccc | ttctstgrga | 480 |
| tcaggactcc | cgttggaata | cagatccaca | gggtacctcc | ctgagatatc | tgacattgta | 540 |
| ccatttctgt | ccccaaatag | aagacggaca | | | | 570 |

<210> SEQ ID NO 17
<211> LENGTH: 126
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (108)
<223> OTHER INFORMATION: Any amino acid

<400> SEQUENCE: 17

Trp Cys Leu Leu Phe Leu Pro Val Leu Leu Thr Val Gly Gly Leu Ser
 1               5                  10                  15

Pro Val Gln Ala Gln Ser Asp Thr Phe Pro Arg Cys Asp Cys Ser Ser
            20                  25                  30

Val Ser Pro Gly Val Leu Ala Gly Ile Val Leu Gly Asp Leu Val Leu
        35                  40                  45

Thr Leu Leu Ile Ala Leu Ala Val Tyr Ser Leu Gly Arg Leu Val Ser
    50                  55                  60

Arg Gly Gln Gly Thr Ala Glu Gly Thr Arg Lys Gln His Ile Ala Glu
65                  70                  75                  80

Thr Glu Ser Pro Tyr Gln Glu Leu Gln Gly Gln Arg Pro Glu Val Tyr
                85                  90                  95

Ser Asp Leu Asn Thr Gln Arg Gln Tyr Tyr Arg Xaa Ala His Ser Met
            100                 105                 110

Pro Ile Ser Gly Leu Met Pro Gly Ser Gly His Ser Arg Cys
        115                 120                 125

<210> SEQ ID NO 18
<211> LENGTH: 2838
<212> TYPE: DNA
<213> ORGANISM: Mus musculus

<400> SEQUENCE: 18

| | | | | | |
|---|---|---|---|---|---|
| acaccaggtc | ccaccagccc | ctggactgtg | gtgtccagtg | catatctggc | caccatgggg | 60 |
| gctctggagc | cctcctggtg | ccttctgttc | cttcctgtcc | tcctgactgt | gtaggtgagt | 120 |
| cggggggctt | ctgtgatgc | ctcctgtgtc | ctcagctcat | gttggggcca | ggactaggca | 180 |
| gagagcagga | agggacagca | cagacaaggg | gaaggctggg | cagaagaagg | ttcctctaga | 240 |

-continued

| | |
|---|---|
| gcctgtgggt ttcaccctga gctagaggcc ctgagatttg aacctggta gtatcagtag | 300 |
| gggggacatt gaagctcaca gatataccta ccacatgttg gtcagtaccg gccgctgggt | 360 |
| gctgtgagac cagctctttc caaccttctt caccttctac atccactgtc tgtgcctcaa | 420 |
| tttacatctt tcttttgaat atagaatcac atatagccca ggctagcttc aaatttgcta | 480 |
| cgtaattgag gataacctca acctttctat tctctgtctc cacctctctc agttacctg | 540 |
| ttcttttctc cttaggatta agtcccgtac aggcccagag tggtaagcca taatacccc | 600 |
| gatctttctc tcttcctctc aaagacctcc tcaggccacc ccttctcctt ctagccctct | 660 |
| ttgtgctaac accaagccct gattgttaac ctgtgtcccc ctcttcatcc tcctgagaca | 720 |
| ctttcccaag atgcgactgt tcttccgtga gccctggtgt actggctggg attgttctgg | 780 |
| gtgacttggt gttgactctg ctgattgccc tggctgtgta ctctctgggc cgcctggtct | 840 |
| cccgaggtca agagagtaag aaggtaaata aatctttaaa aaaaattgtc ccagtcccca | 900 |
| gcttagtcct tcttcacacc atatgtcact ctctatccct ctctagggac ccggaaacaa | 960 |
| cacattgctg agactgagtc gccttatcag gtaagaacgc caaattcttc tccacccttg | 1020 |
| ctcctgcccc gtcctggcta tcccctccc cagtacagac acagacaa acacacacac | 1080 |
| acaaatacac agagacatat ataaacacac tcacataaat aaacacacac atacctac | 1140 |
| acacacacac acacatacct acacacacac acacacatac ctacacacac acacacac | 1200 |
| acacacacac actaccttc ccagaacctt aaggtccctt cctcaggagc tcccccaatc | 1260 |
| ctgaaggcaa aggactaact gtcaaacata ttcggtggtc aaccatgacc tttaagctca | 1320 |
| gcttctaatg agtctcttgt caagattcta ttcctctgtc tctctctctc tctctctctc | 1380 |
| tctctctctc tctctctctc tctctctctc tctgcgtgtg tgtgtgtgtg tgtgtgtgtg | 1440 |
| tgtgtaggca ggttataaga ggacatcaaa tcctatcttt accttatttt taaaatggca | 1500 |
| ctgattttgc tctgtattta catgtgtgtg tggagcaggt gtgcatatgc actggcagcc | 1560 |
| atgtggggt cagaagacaa cccgtggggg ctggttctct ccttccacct tgtggatctc | 1620 |
| tgaactctaa attctagttg tcaagcttgg cagcaagtgc tttacccact gaaccatctc | 1680 |
| accagcccca agcctccttc ctaacctttg ggctctgggt gaggctatgt ctctagggaa | 1740 |
| acacacacca ggctggtctc tggtacatgc tctcagagac tctgcccctg ggaggcacag | 1800 |
| acccctgctc tgtgacccaa tttctggaag tctacctccc tccctgtagc cagttttgcc | 1860 |
| cattcgactg actccttgct ggaggaactt tttctctgaa aagtgttaga atctcttgat | 1920 |
| tcttgttttg agtttggtgt ggggaagtag tggcgtgtgt ctttaatccc agcgctctgg | 1980 |
| tggcagaggt aggcagatct ctgtgaattt gaggctggcc tggtctacag tgtgagttcc | 2040 |
| tggacaggca gggctaccca agaaaccct gtctacaagc aaacaaacaa acaaaaacaa | 2100 |
| aacaaaacaa aaagaatct caatattggc catctgatgt ccagaagacc ccgggctgtc | 2160 |
| tagtttctga gagccaggaa actttagggc aaatgtcagc ctgattttt tatccttcgg | 2220 |
| tatcttggtt gaggcctaca tggatcaaca cagcactcca attggagaag cttatttgaa | 2280 |
| gcaacttaac aaaatcattt ggggtgacat tatgaagaga ttgaagtgaa ccaatataat | 2340 |
| ggtgggacag gaaagaaact gaagatgggg aaactaaaac attgccaaga ctcaaagggt | 2400 |
| gagcaggttg aagatctgtg ggcttggtgc tccaggcatc ggggtggggg gctgcacatg | 2460 |
| taaggaccct gggggttggtg cctaatgtgc aggcagaaag gccaggagaa tgctgagtgc | 2520 |
| atttgaataa aatcttgacc ttttcatgat tttaagtttg aaaaacctgc cagagacctt | 2580 |

-continued

```
gaaggtcatt aggaggctag atttgttttt atttgctggg cccctccaa tgatggcctt    2640 tttttttttt tttaaggagc ttcagggtca gagaccagaa gtatacagtg acctcaacac    2700
acagaggcaa tattacagat gagcccactc tatgcccatc agcggcctga tgcccggatc    2760
cggtcattcc agatgcctac tcaacaagcc ctctctgaga tcaggactcc cgttggaata    2820
cagatccaca gggtacct                                                  2838
```

```
<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 19
ggctctggag ccctcctggt gc                                               22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 20
actctgggcc tgtacgggac t                                                21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 21
agtcccgtac aggcccagag t                                                21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 22
cagagtcaac accaagtcac c                                                21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 23
ggtgacttgg tgttgactct g                                                21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 24
```

```
ctcagtctca gcaatgtgtt g                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
caacacattg ctgagactga g                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 26
ctgtgtgttg aggtcactgt a                                              21

<210> SEQ ID NO 27
<211> LENGTH: 452
<212> TYPE: DNA
<213> ORGANISM: Mus musculus
<220> FEATURE:
<221> NAME/KEY: CDS
<222> LOCATION: (1)..(333)

<400> SEQUENCE: 27 atg ggg gct ctg gag ccc tcc tgg tgc ctt ctg ttc ctt cct gtc ctc     48
Met Gly Ala Leu Glu Pro Ser Trp Cys Leu Leu Phe Leu Pro Val Leu
 1               5                  10                  15 ctg act gtg gag gga tta agt ccc gta cag gcc cag agt gac act ttc     96
Leu Thr Val Glu Gly Leu Ser Pro Val Gln Ala Gln Ser Asp Thr Phe
            20                  25                  30 cca aga tgc gac tgt tct tcc gtg agc cct ggt gta ctg gct ggg att    144
Pro Arg Cys Asp Cys Ser Ser Val Ser Pro Gly Val Leu Ala Gly Ile
        35                  40                  45 gtt ctg ggt gac ttg gtg ttg act ctg ctg att gcc ctg gct gtg tac    192
Val Leu Gly Asp Leu Val Leu Thr Leu Leu Ile Ala Leu Ala Val Tyr
    50                  55                  60 tct ctg ggc cgc ctg gtc tcc cga ggt caa gag agg acc cgg aaa caa    240
Ser Leu Gly Arg Leu Val Ser Arg Gly Gln Glu Arg Thr Arg Lys Gln
65                  70                  75                  80 cac att gct gag act gag tcg cct tat cag gag ctt cag ggt cag aga    288
His Ile Ala Glu Thr Glu Ser Pro Tyr Gln Glu Leu Gln Gly Gln Arg
                85                  90                  95 cat gaa gta tac agt gac ctc aac aca cag agg caa tat tac aga        333
His Glu Val Tyr Ser Asp Leu Asn Thr Gln Arg Gln Tyr Tyr Arg
               100                 105                 110 tgagcccact ctatgcccat cagcggcctg atgcccggat ccggtcattc cagatgccta   393
ctcaacaagc cctctctgag atcaggactc ccgttggaat acagatccac agggtacct    452

<210> SEQ ID NO 28
<211> LENGTH: 111
<212> TYPE: PRT
<213> ORGANISM: Mus musculus

<400> SEQUENCE: 28

Met Gly Ala Leu Glu Pro Ser Trp Cys Leu Leu Phe Leu Pro Val Leu
```

```
                1               5                  10                 15
Leu Thr Val Glu Gly Leu Ser Pro Val Gln Ala Gln Ser Asp Thr Phe
                    20                 25                 30

Pro Arg Cys Asp Cys Ser Ser Val Ser Pro Gly Val Leu Ala Gly Ile
            35                 40                 45

Val Leu Gly Asp Leu Val Leu Thr Leu Leu Ile Ala Leu Ala Val Tyr
        50                 55                 60

Ser Leu Gly Arg Leu Val Ser Arg Gly Gln Glu Arg Thr Arg Lys Gln
 65                 70                 75                 80

His Ile Ala Glu Thr Glu Ser Pro Tyr Gln Glu Leu Gln Gly Gln Arg
                85                 90                 95

His Glu Val Tyr Ser Asp Leu Asn Thr Gln Arg Gln Tyr Tyr Arg
            100                105                110
```

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 29
ccgctcgagg gcttcatggg gggacttgaa c                                    31

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 30
ctagtctaga ggatccaggt atcattgtgc tgactgtcat gattcg                    46

<210> SEQ ID NO 31
<211> LENGTH: 431
<212> TYPE: DNA
<213> ORGANISM: Mus musculus

<400> SEQUENCE: 31
ggcttcgttt tctgttctgc gccgttacag atccaagctc ctcgagggct tcatgggggg     60
acttgaaccc tgcagcaggc tcctgctcct gcctctcctg ctggctgtaa gtggtctccg    120
tcctgtccag gcccaggccc agagcgattg cagttgctct acggtgagcc cgggcgtgct    180
ggcagggatc gtgatgggag acctggtgct gacagtgctc attgccctgg ccgtgtactt    240
cctgggccgg ctggtccctc gggggcgagg ggctgcggag gcagcgaccc ggaaacagcg    300
tatcactgag accgagtcgc cttatcagga gctccagggt cagaggtcgg atgtctacag    360
cgacctcaac acacagaggc cgtattacaa atgagcccga atcatgacag tcagcacaat    420
gatacctgga t                                                         431

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Tyr Asn Glu Leu Asn Leu Gly Arg Arg Glu Glu Tyr Asp Val Leu
 1               5                  10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Asn Glu Leu Gln Lys Asp Lys Met Ala Glu Ala Tyr Ser Glu Ile
 1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Gln Gly Leu Ser Thr Ala Thr Lys Asp Thr Tyr Asp Ala Leu
 1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Gln Pro Leu Lys Asp Arg Glu Asp Gln Tyr Ser His Leu
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Gln Pro Leu Arg Asp Arg Asp Asp Ala Gln Tyr Ser His Leu
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Glu Pro Ile Arg Lys Gly Gln Arg Asp Leu Tyr Ser Gly Leu
 1               5                  10                  15

<210> SEQ ID NO 38
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 38

Tyr Glu Asp Ile Ser Arg Gly Leu Gln Gly Thr Tyr Gln Asp Val
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Glu Gly Leu Asp Ile Asp Gln Thr Ala Thr Tyr Glu Asp Ile
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Thr Gly Leu Asp Thr Arg Asn Gln Glu Thr Tyr Glu Thr Leu
 1               5                  10                  15

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Glu Glu Leu Asn Ile Tyr Ser Ala Thr Tyr Ser Glu Leu
 1               5                  10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Gln Glu Leu Gln Gly Gln Arg His Glu Val Tyr Ser Asp Leu
 1               5                  10                  15

<210> SEQ ID NO 43
<211> LENGTH: 109
<212> TYPE: PRT
<213> ORGANISM: Mus musculus

<400> SEQUENCE: 43

Met Gly Ala Leu Glu Pro Ser Trp Cys Leu Leu Phe Leu Pro Val Leu
 1               5                  10                  15

Leu Thr Val Leu Gly Leu Ser Pro Val Gln Ala Gln Ser Asp Thr Phe
                20                  25                  30

Pro Arg Cys Asp Cys Ser Ser Val Pro Gly Val Leu Ala Gly Ile Val
```

-continued

```
                35                  40                  45

Leu Gly Asp Leu Val Leu Thr Leu Leu Ile Ala Leu Ala Tyr Ser Leu
         50                  55                  60

Gly Arg Leu Val Ser Arg Gly Gln Glu Arg Thr Arg Lys Gln His Ile
 65                  70                  75                  80

Ala Glu Thr Glu Ser Pro Tyr Gln Glu Leu Gln Gly Gln Arg Pro Glu
                 85                  90                  95

Val Tyr Ser Asp Leu Asn Thr Gln Arg Gln Tyr Tyr Arg
                100                 105

<210> SEQ ID NO 44
<211> LENGTH: 111
<212> TYPE: PRT
<213> ORGANISM: Mus musculus

<400> SEQUENCE: 44

Met Gly Ala Leu Glu Pro Ser Trp Cys Leu Leu Phe Leu Pro Val Leu
  1               5                  10                  15

Leu Thr Val Glu Gly Leu Ser Pro Val Gln Ala Gln Ser Asp Thr Phe
                 20                  25                  30

Pro Arg Cys Asp Cys Ser Ser Val Ser Pro Gly Val Leu Ala Gly Ile
             35                  40                  45

Val Leu Gly Asp Leu Val Leu Thr Leu Leu Ile Ala Leu Ala Val Ile
 50                  55                  60

Ser Leu Gly Arg Leu Val Ser Arg Gly Gln Glu Arg Thr Arg Lys Gln
 65                  70                  75                  80

His Ile Ala Arg Thr Glu Ser Pro Tyr Gln Glu Leu Gln Gly Gln Arg
                 85                  90                  95

Pro Glu Val Tyr Ser Asp Leu Arg Thr Gln Arg Gln Tyr Tyr Arg
                100                 105                 110
```

POLYPEPTIDES ASSOCIATED WITH ACTIVATORY RECEPTORS AND THEIR BIOLOGICAL APPLICATIONS

The present application is a continuation of U.S. application Ser. No. 10/645,539, filed Aug. 22, 2003, now abandoned which is a divisional of U.S. application Ser. No. 09/403,980, filed Jan. 19, 2000, now abandoned which is a 371 U.S. national phase of PCT/FR98/00883, filed Apr. 30, 1998, which designated the U.S., the entire contents of each of which is hereby incorporated by reference.

The invention relates to new particular polypeptides capable of transducing a signal originating from an activatory receptor for class I MHC molecules, functioning both as an autonomous receptor or as a co-receptor, and a KAR (Killer-cell Activatory Receptor), in particular to the antibodies obtained from said polypeptides serving as immunogens, and to the nucleic acids corresponding to said polypeptides.

The invention also relates to the processes for obtaining such polypeptides and to the biological, more particularly, preventive, therapeutic and diagnostic applications, of said polypeptides, antibodies and nucleic acids.

In order to maintain the coherence and to ensure the integrity of the body, the immune system must bring into play a coordinated system of intercellular communications.

Different types of receptors are involved in these communications. Three of them, namely the receptors for the antigen of B lymphocytes (BCR), the receptors for the antigen of T lymphocytes (TCR) and the receptors recognizing the Fc portion of antibodies (RFc), are now well described and their different structures are relatively well known.

Other receptors which are neither receptors for antigens, nor receptors for antibodies have been described but their structures and action mechanisms are still little known.

These are the receptors for molecules of MHC (Major Histocompatibility Complex) such as KARs (Killer cell Activatory Receptors) and their inhibitory counterparts, KIRs (Killer cell Inhibitory Receptors).

KARs and KIRs are not limited to NK cells: they are also naturally expressed by T cells.

KARs are highly homologous with KIRs (up to 96% homology between KARs and KIRs at the extracytoplasmic level).

However, KARs and KIRs do not perform the same functions: KIRs are involved in the negative (inhibitory) control of the activation of NK and T cells, whilst KARs are involved in the positive (stimulatory) control of the activation of NK and T cells.

Major differences as regards the trans- and intracytoplasmic domains were demonstrated between the activatory isoform (KAR) and inhibitory isoform (KIR).

In fact, unlike KIRs, KARs express a charged amino acid residue (lysine) in their transmembrane domain and do not contain an ITIM unit (immunoreceptor inhibition unit based on tyrosine residue(s)) in their intracytoplasmic domain. For all that the monomeric KAR receptors do not contain an ITAM unit (immunoreceptor activation unit based on tyrosine residue(s)).

The situation observed for KARs, activatory receptors for MHC molecules, and members of the IgSF (immunoglobulins superfamily), namely an activatory receptor, counterpart of an ITIM inhibitory receptor, itself presenting neither ITIM, nor ITAM but presenting a transmembrane charged amino acid (lysine, arginine, aspartic acid, glutamic acid), can be observed for other types of receptors. This is so for the case of activatory (or at the very least non inhibitory) receptors for MHC molecules, such as NKG2C/D (which is of lectin type and the inhibitory counterpart of which is NKG2A/B), but also for other non inhibitory receptors, such as SIRP β and ILT 1, the ligands of which are still unknown and which have been described either as hematopoietic cells and on non-hematopoietic cells (SIRP β), or on B cells, macrophages and dendritic cells (ILT1).

KARs can function as autonomous receptors, in particular for class I MHC molecules. Thus it is known that the engagement of KARs with class I MHC molecules expressed on the surface of target cells, initiates the lymphocyte activation programmes as established by the fact of $Ca^{2+}$ intracytoplasmic mobilisation and the induction of lysis of the target cells.

In addition to their functions as autonomous receptors for MHC molecules, KARs can also perform co-receptor functions for TCR and RFc receptors (Mandelboim O. et al., 1996, *Science* 274:2097; Cambiaggi A. et al., 1996, *Blood* 87:2369).

In fact, during the recognition of constant fragments (cF) of immunoglobulins G (IgG) by receptors such as CD16 (RFcγIII), and during the recognition of antigens by the CD3/TCR complex restricted by class I or II MHC molecules, KARs can play the role of co-receptors and thus augment the intensity of the cell response, in particular faced with small quantities of antigens, maintain the cell response over time, and also cooperate in the stimulation of cell proliferation.

The role of KARs, naturally expressed on NK and T lymphocyte sub-populations, is not restricted by their own ligands, namely the class I MHC molecules, but extends to the equilibrium of the immune system generally.

The functioning of naturally expressed KARs therefore influences the proliferation of NK and T cells, the production by these cells of cytokine type substances, the lysis of target cells such as deleterious autologous cells, malignant cells or cells infected by viruses, allogenic cells, but also the tolerance of the immune system faced with certain antigens.

Any non- or dys-functioning of KARs can therefore lead to different diseases or undesired reactions, all associated with the functioning of the immune system, such as immuno-deficiency diseases, auto-immune diseases (e.g. multiple sclerosis), tumors, viral, bacterial, parasitic and allergies, graft rejections. For example, it has been shown that if a person only displays less than 10% of lymphocytes expressing KARs, nearly all the lymphocytes of patients suffering from LDGL (lymphoproliferative disease of the granular lymphocytes) express KARs.

A purpose of the present invention is to provide means allowing the diagnosis of an abnormal or undesired functioning of activatory receptors for class I MHC molecules such as KARs and to control their functioning.

Thus a subject of the invention is new polypeptides, called below KARAP (KAR-Associated Proteins), which are necessary for transducing a signal originating for a KAR, as well as the antibodies and nucleic acids obtained from said new polypeptides. A subject of the invention is also a process for obtaining said new polypeptides as well as their biological applications.

By "KAR receptor", is meant, in the present invention, human receptors of immunoglobulin type which are non-inhibitory counterparts of KIR receptors, such as KAR p50 (KIRIIDS1 to KIRIIDS5), KIRIIIDS1 receptors, but also non-inhibitory receptors with a similar structure to these KAR receptors, and in particular human receptors of lectin type such as NKG2C, NKG2D (naturally expressed on NK and T cells), murine receptors of immunoglobulin type such as pir A (naturally expressed on myeloid cells, B cells), gp49A (naturally expressed on mastocytes), murine receptors of lectin type such as Ly49D, Ly49H (naturally expressed on NK and T cells).

By KARAP polypeptide is therefore meant any isolated polypeptide (other than a KAR) in the absence of which said KAR receptor is naturally incapable of transducing a detectable activatory signal. This does not exclude the fact that a determined KARAP polypeptide may not only be associated with a KAR receptor as defined above, but also with other activatory or non-inhibitory monomeric receptors with a structure close to that of KARs as defined above, and in particular with a human activatory receptor of immunoglobulin type of the LIR/MIR/ILT family such as ILT1.

The term "polypeptide" includes, in the present Application, not only said polypeptide, but also the homologues of this polypeptide, as obtained by deletion, insertion, inversion or preservative substitution of amino acids, and the fragments of this polypeptide, as obtained by hydrolysis of said polypeptide using proteases, said homologues or fragments being capable of transducing a signal originating a KAR. This term "polypeptide" covers, in the present Application, both polypeptides and proteins.

A polypeptide according to the invention is necessary for transducing the signal received by a KAR receptor: therefore it is an isolated polypeptide which allows the restoration of a deficient KAR activation. In order to determine whether a given isolated polypeptide allows the restoration of a deficient KAR activation, a person skilled in the art can proceed by showing that a KAR receptor exists which, if it is expressed by an appropriate cell in the absence of this polypeptide, does not succeed in transducing a detectable activatory signal, or does not succeed in transducing an activatory signal which is satisfactory for the envisaged application. A version of this determination is presented in Example 3 below by comparison between the activation capacity (release of serotonin) of an RBL-2H3 cell expressing the KAR p50.2 receptor only, and that of an RBL-2H3 cell which at one and the same time expresses the KAR p50.2 receptor and its KARAP polypeptide. Examples of appropriate cells are presented in FIG. 5 below.

By "restored deficient KAR activation KAR", is meant that the transduction at the cell, of a significant activatory signal, by said KAR is possible, or, if appropriate, satisfactory. In particular, this can be tested using cellular stimulation by antibodies.

In order to determine at the level of a cell whether a signal originating from a KAR is or is not transduced, and to determine whether such a signal is stimulated or inhibited, numerous means are at the disposal of a person skilled in the art. Examples of such means include the stimulation of said KAR by a ligand and measurement of the cytokines secreted (cf. for example, Cambiaggi et al. 1996, Blood 87:2369), of cell proliferation (cf. for example Mandelboim et al. 1996, Science 274:2097), of cytotoxicity (cf. for example the redirected cytotoxicity test described below), of mobilization of intracytoplasmic calcium (cf. for example Blery et al., 1997, J. Biol. Chem. 272, 8989-8996), and/or of the induction of phosphorylation (cf. for example Vivier et al. 1991, J. Immunol. 146:206).

A polypeptide according to the invention is in addition characterized in that it is capable of associating with a KAR, and of not associating with the inhibitory counterpart of this KAR.

Methods allowing determination of whether a polypeptide is capable of associating with a KAR, and of not associating with the inhibitory counterpart of this KAR (i.e. of not associating with a corresponding KIR receptor), are well known to a person skilled in the art. An example of such a method comprises in particular:

expression of this polypeptide at a KAR$^+$ KIR$^-$ cell on the one hand, and at a KAR$^-$ KIR$^+$ cell, immunoprecipitation of one or more polypeptide fraction(s) from the lysate of these cells with at least anti-KAR and/or anti-KIR antibodies, observation of the presence of said polypeptide in the fraction(s) originating from the KAR$^+$ KIR$^-$ cell, and the absence of this same polypeptide from the fraction or fractions originating from the KAR$^-$KIR$^+$ cell. Examples of anti-KIR and/or anti-KAR antibodies include anti-CD158, anti-p70/NKB1, anti-p140 antibodies and more particularly the EB6, GL183 or PAX250 monoclonal antibodies. A method allowing the expression of such a polypeptide by a cell is indicated in Example 3 below.

A KARAP polypeptide according to the invention can moreover be characterized in that it is obtained:

i. by immunoprecipitation of one or more polypeptide fractions of lysates of cells expressing KAR receptors capable of transducing an activatory signal, with the help of one or more anti-KIR and/or anti-KAR antibodies such as an anti-CD158, anti-p70/NKB1 or anti-p140 antibody and more particularly the EB6, GL183 or PAX250 monoclonal antibody, ii. it being possible for each polypeptide fraction optionally to be exhausted beforehand by removal of the fractions immunoprecipitated with the help of anti-CD3$\zeta$ and/or anti-FcεRIγ antibodies, and/or to be reprecipitated with the help of one or more anti-KIR and/or anti-KAR antibodies such as an anti-CD158, anti-p70/NKB1, anti-p140 antibody and more particularly the EB6, GL183 or PAX250 monoclonal antibody, iii. by resolution of the polypeptides of said polypeptide fraction(s) according to their molecular weight, and recovery of the polypeptides corresponding to a molecular weight of about 12±2 kDa, or by resolution of the polypeptides of said polypeptide fraction(s) according to their molecular weight having subjected said polypeptide fraction(s) to a kinase test, and recovery of the phosphorylated polypeptides corresponding to a molecular weight of about 12, 14 and/or 16±2 kDa. The kinase test can be carried out as described below in the examples (cf. material and methods of Example 1 below).

Said cells expressing KAR receptors capable of transducing an activatory signal can be in particular NK cells and/or T cells and/or myeloid cells and/or B cells and/or mastocytes. Means for determining whether a KAR is capable or not of transducing a signal to the cell have been indicated above.

A KARAP polypeptide according to the present invention is, in addition, characterized in that its amino acid sequence:

has at least one phosphorylatable tyrosine amino acid, has a molecular weight comprised between about 10±2 and 16±2 kDa (in particular, real molecular weight of 10±2 kDa, apparent molecular weight on polyacrylamide gel under denaturing conditions of 12±2 to 16±2 kDa according to the degree of phosphorylation).

In addition it is characterized in that its amino acid sequence comprises at least one ITAM YxxL/Ix$_{6-8}$YxxL/I unit in the intracytoplasmic region.

According to one aspect of the invention, the amino acid sequence of a KARAP polypeptide comprises an extracytoplasmic region, a transmembrane region, and/or a entracytoplasmic region. In a characteristic manner, this intracytoplasmic region is in the majority relative to the other regions of the sequence of this polypeptide. Means for identifying the extracytoplasmic, transmembrane, intracytoplasmic regions are known to a person skilled in the art (for example, hydropathicity algorithms, formation of inverse vesicles).

According to another aspect of the invention, the amino acid sequence of a KARAP polypeptide contains at least one extracytoplasmic cysteine amino acid.

According to yet another aspect of the invention, the amino acid sequence of a KARAP polypeptide contains at least one transmembrane charged amino acid (R, K, D, E).

The polypeptides according to the invention can be phosphorylated at the level of at least one tyrosine residue, or be non phosphorylated.

In one embodiment of the invention, said polypeptides are presented in the form of dimers linked by a disulphide bridge; they associate in a selective and non covalent manner with KARs which function, either as autonomous receptors for class I MHC molecules, or as co-receptors of TCR or of an RFc such as CD16.

According to an advantageous aspect of the invention, a KARAP polypeptide is capable of binding to a molecule having an SH2 domain such as ZAP-70, p72$^{syk}$, p56$^{lck}$, p59$^{fyn}$, p60$^{fyn}$, Grb-2, pp36-38 (lat), PLC-α1, p85 (PI-3 kinase), Shc, or to a molecule having a PTB domain (PhosphoTyrosine Binding) such as Shc. Such a binding can be observed by incubation of polypeptides according to the invention with molecules having an SH2 or PTB domain and measurement of the plasmon resonance (Olcese et al. 1996, The Journal of Immunology 156:4531-4534).

A particular KARAP polypeptide according to the invention has an amino acid sequence essentially constituted by SEQ ID no 2. The present invention also relates to polypeptides the sequence of which is essentially constituted by the extracytoplasmic part of SEQ ID no 2, namely SEQ ID no 3, or by the transmembrane part of SEQ ID no 2, namely SEQ ID no 4, or the intracytoplasmic part of SEQ ID no 2, namely SEQ ID no 5. Other particular KARAP polypeptides according to the invention have an amino acid sequence essentially constituted by SEQ ID no 11, no 12, no 13, no 14, no 15, no 17 (consensus sequence of the KARAP protein of mouse C57Bl/6), or no 28 (protein sequence of the KARAP of mouse 129 obtained from the genomic sequence).

Such polypeptides can also be obtained, after sequencing, by chemical synthesis or using recombinant DNA techniques.

Said KARAP polypeptides are necessary for transducing signals originating from activatory receptors, the KARs, which have neither intracytoplasmic ITIM nor ITAM but which have a transmembrane amino acid residue.

According to an advantageous provision, the polypeptides according to the invention are modified by glycosylation, phosphorylation, sulphonation, biotinylation, acylation, esterification, or by addition, substitution or suppression of entities having a molecular shape similar to that of phosphate groups, such as phosphonate, by the addition of tracer reagents such as luciferase, GFP (Green Fluorescence Protein) or analogues thereof, by the addition of purification targets such as an affinity ligand, or by the addition of entities modifying its solubility. Modifications of particular benefit include those which modify said polypeptide so as to block or inhibit its capacity to transduce the signal received (negative transdominant strategy). A polypeptide according to the invention, in a form modified in this way, is used in particular in any composition or method intended to modulate in a negative manner (inhibit) a given immune response, in particular an undesired or abnormal immune response (for example, autoimmune diseases, allergies, graft rejection). Thus appropriate modifications include those which render the phosphorylation on tyrosine of said polypeptide non hydrolysable under biological conditions (for example, by the addition of phosphonate groups). They also include those which render non functional an amino acid residue which is critical to the functioning of a polypeptide according to the invention: for example, by substitution or mutation of a tyrosine residue (Y), in particular a tyrosine residue contained in an ITAM unit, into a phenylalanine residue (F), which hinders the binding of said polypeptide thus modified to a protein having an SH2 or PTB domain.

According to another advantageous provision, the polypeptides of the invention, their fragments, homologues, or modified forms are capable of crossing a cell membrane, i.e. double lipidic layer.

The present invention also relates to antibodies, in particular monoclonal antibodies, and the fragments of such antibodies, in particular the Fc, Fv, Fab, F(ab)'$_2$, CDR fragments, as obtained by immunogenesis from a KARAP polypeptide according to the invention, or as obtained from a fragment, homologue or modified form of such a polypeptide.

In particular a subject of the invention is fragments of such antibodies, in particular an Fc, Fv, Fab, F(ab)'$_2$, CDR fragment, as obtained by immunogenesis from a polypeptide the sequence of which is essentially constituted by the extracytoplasmic, intracytoplasmic, or transmembrane part of such a KARAP polypeptide according to the invention. In particular it relates to antibodies capable of recognising, according to an antigen-antibody type reaction, SEQ ID no 2, SEQ ID no 3, SEQ ID no 4, SEQ ID no 5, SEQ ID no 11, SEQ ID no 12, SEQ ID no 13, SEQ ID no 14, SEQ ID no 15, SEQ ID no 17 and/or SEQ ID no 28, as well as their fragments.

Such antibodies are obtained by the immunization of animals, such as rabbits and mice, against polypeptides, fragments, homologues or forms modified according to the invention as essentially obtained by elution of electrophoretic bands, by chemical synthesis or by a soluble fusion protein technique (GST), said polypeptides, fragments, homologues or modified forms being optionally coupled to immunogens such as ovalbumin.

Monoclonal antibodies are then produced by hybridomal fusion of lienal immune cells, screening and purification of the culture supernatants (Köhler and Milstein, 1975, Nature 256, 495-497; Antibodies, a laboratory manual, 1988, Harlow and David Lane, Ed. Cold Spring Harbor laboratory).

From these antibodies, diantibodies can be generated according to standard procedures. Said fragments can, if necessary, be inserted in or grafted to humanizing structures.

The present invention also relates to the nucleic acids containing a sequence corresponding to the open reading frame, according to the universal genetic code, and taking into account the degeneration of said code, the amino acid sequence of a polypeptide, fragment, or homologue according to the invention, as well as the variants which have a homology greater than or equal to 60% with such nucleic acids, and which are capable of coding for a molecule transducing an activatory signal originating from a KAR as defined above. In particular it relates to any nucleic acid the DNA sequence of which is essentially constituted by SEQ ID no 1 (cDNA of the mature KARAP protein of sequence SEQ ID no 2), no 6, no 7, no 8, no 9, no 10, no 16 (consensus cDNA sequence of KARAP of mouse C57Bl/6), no 27 (cDNA sequence of KARAP of mouse 129 obtained from the genomic sequence), no 18 (genomic sequence of KARAP of mouse 129), or no 31 (cDNA sequence of human KARAP), or by any part corresponding to the extra-, intra-cytoplasmic and/or transmembrane regions of these sequences, or by any part corresponding to an exon or an intron of these sequences.

The present invention also relates to a process for obtaining a polypeptide according to the invention comprising the following stages:

i. immunoprecipitation of one or more polypeptide fraction(s) of lysates of cells expressing functional KAR receptors (for example NK cells and/or T cells and/or myeloid cells and/or B cells and/or mastocytes) using one or more anti-KIR and/or anti-KAR antibodies, such as an anti-CD158, anti-p70/NKB1, anti-p140 antibody, and more particularly the monoclonal EB6, GL18.3 or PAX250 antibodies, ii. it being possible for each polypeptide fraction optionally to be exhausted beforehand by removal of the fractions immunoprecipitated with the help of anti-CD3 and/or anti-FcεRIγ antibodies, and/or to be reprecipitated with the help of one or more anti-KIR and/or anti-KAR antibodies such as an anti-CD158, anti-p70/NKB1, anti-p140 antibody and more particularly the EB6, GL183 or PAX250 monoclonal antibody, iii. separation of the polypeptides from said polypeptide fraction(s) according to their molecular weight and recovery of the polypeptides corresponding to a molecular weight of approximately 12±2 kDa, or separation of the polypeptides of said polypeptide fraction(s) according to their molecular weight having subjected said polypeptide fraction(s) to a kinase test, and recovery of the phosphorylated polypeptides corresponding to a molecular weight of approximately 12, 14 and/or 16±2 kDa.

A subject of the present Application is also a method for obtaining the sequence of particular KARAP polypeptides according to the invention. This method, a version of which is described in Example 2 below (bio-informatics strategies), includes in particular the screening of those of the polypeptide sequences which correspond to the following criteria:

the sequence has at least one phosphorylable tyrosine amino acid, the sequence has a molecular weight between approximately 5 and 25 kDa, the sequence comprises an extracytoplasmic region, a transmembrane region, and an intracytoplasmic region, the sequence has at least one cysteine amino acid in its extracytoplasmic region, the sequence includes at least one charged amino acid (R, K, D, E) in its transmembrane region, and the sequence includes at least one ITAM $YxxL/Ix_{6-8}YxxL/I$ unit in its intracytoplasmic region, the polypeptide corresponding to the selected sequence must be capable of associating with a KAR, and not associating with the corresponding inhibitory counterpart receptor (KIR), as defined above.

A subject of the present Application is also a method for determining or checking whether a candidate polypeptide corresponds to a KARAP polypeptide according to the invention. An embodiment of such a method is given in Example 2 below. Such a method consists of producing an antibody against a characteristic part of this candidate polypeptide (for example an intracytoplasmic region comprising at least one ITAM unit or an extracytoplasmic region), and to check that a KAR receptor exists which, when it is expressed functionally on a cell, is combined with a recognized element, according to a reaction of antigen-antibody type, by said antibody.

This method, according to the invention, of identifying KARAP polypeptides thus consists in particular of:

producing a mono- or polyclonal antibody directed against this candidate polypeptide, and in particular against an extracytoplasmic region of this candidate polypeptide and/or a region which comprises at least one ITAM unit (for example, in the case of the mouse KARAP protein SEQ ID no. 2 identified above, an antibody directed against a region of the extracytoplasmic part (SEQ ID no. 3) or of the intracytoplasmic part (SEQ ID no. 5) of SEQ ID no. 2), brining this antibody into contact with a lysate of cells, possessing, in a functional form, the activatory or non-inhibitory receptor for which the candidate polypeptide is supposed to continue the KARAP, under mild conditions allowing binding reactions of antigen-antibody type, identifying the candidate polypeptide as being a KARAP polypeptide according to the invention when, in any reaction products formed, there are a product having an apparent molecular weight close to that of said activatory or non-inhibitory receptor (approximately 50 kDa for the KAR p50) and a product having an apparent molecular weight close to that of the candidate polypeptide (in particular between approximately 10 and 16 kDa).

This identification method according to the invention can in particular be carried out:

by bringing said antibody into contact as described above, precipitating any reaction products formed under mild detergent conditions maintaining the molecular complexes (for example 1% digitonin, see Example 1 above), measuring the molecular weight of the precipitated products, for example by electrophoretic migration in the presence of the markers of molecular weight on a polyacrylamide gel under denaturing conditions, and identifying the candidate polypeptide as being a KARAP polypeptide according to the invention as described above.

The present invention also relates to a pharmaceutical composition comprising, in conjunction with a pharmaceutically acceptable vehicle, an effective quantity of at least one polypeptide, KARAP, fragment, homologue or form modified according to the invention, at least one antibody or fragment of antibody according to the invention, or at least one nucleic acid or nucleic acid variant according to the invention.

The pharmaceutical composition according to the invention can be formulated in solid or liquid form or in the form of a suspension, for oral, parenteral, topical, intravaginal, intrarectal administration or for oral and/or nasal inhalation.

Said pharmaceutical composition according to the invention is intended to modulate the activity of a KAR. In order to stimulate the activity of a KAR, said pharmaceutical composition will comprise agents facilitating the transduction of the signal originating from said KAR, such as, for example, polypeptides, fragments, homologues, or nucleic acids, variants according to the invention capable of crossing a double lipidic layer. In order to inhibit the activity of a KAR, said pharmaceutical composition will comprise agents blocking the transduction of the signals originating from said KAR such as, for example, fragments of antibodies according to the invention capable of crossing a double lipidic layer in order to block the cellular KARAPs, or modified polypeptides, according to the invention, phosphorylated or not, for example by phosphorylation not hydrolysable under biological conditions, in order to block proteins with an SH2 (ZAP-70, $p72^{syk}$) or PTB domain or any molecule which adapts or carries out the activation of said KAR. Such modifications include in particular the addition of phosphonate groups, and/or the mutation of at least one Tyrosine residue (Y) into a phenylalanine residue (F).

The present Application therefore relates to a composition for the prevention, the reduction, and/or the treatment of an abnormal or undesired functions of a cell involved in an immune reaction. Such a composition advantageously includes polypeptides, or, if appropriate, modified polypeptides according to the invention.

In order to determine at the level of a cell whether a signal originating from a KAR is or is not transduced, and to determine whether such a signal is stimulated or inhibited, numerous means are at the disposal of a person skilled in the art. Examples of such means have been indicated above.

The use of said polypeptides, antibodies and nucleic acids as diagnostic agents, also falls within the scope of the present invention (diagnostic methods, and diagnostic kits permitting their implementation).

The present invention also relates to a method of in vitro diagnosis of abnormal or undesired functioning of a cell, comprising the following stages:
   bringing at least one cell, or cell extract, into contact with
      an antibody according to the invention, or a fragment of such antibody, or with a nucleic acid according to the invention or a variant of such nucleic acid, and
   revealing any reaction product formed.

The stage of bringing into contact is carried out under conditions in particular of duration, temperature, buffer, where appropriate gel crosslinking, allowing the establishment of a reaction of antigen-antibody type for example by ELISA (Enzyme Linked Immunoabsorbent Assay), or where appropriate, of a reaction of nucleic acids hybridization and PCR type (polymerase chain reaction).

For the revelation of any reaction product formed, tracers can be used such as fluorescent, enzymatic, radioactive or luminescent tracers.

Said in vitro diagnostic method according to the invention allows the diagnosis of abnormal or undesired cellular functioning which can manifest themselves as an immunoproliferative disease, an immunodeficiency disease such as an HIV disease, a cancer such as lymphoproliferative disease of the granular lymphocytes, an auto-immune disease such as rheumatoid arthritis, an infectious disease such as malaria, an allergic response, a transplant rejection.

The present invention also relates to a method for identifying molecules which adapt or carry out the activation of a KAR, and to a method for identifying molecules capable of modulating a cell activity resulting from the activation of a KAR.

Said method for identifying molecules which adapt or carry out the activation of a KAR according to the invention comprises the following stages:
   i. bringing the candidate molecules into contact with the polypeptides according to the invention (or with fragments or homologues of such polypeptides), and
   ii. selecting those candidate molecules for which a binding with said polypeptides (or with said fragments of polypeptides) is observed.

The candidate molecules likely to be molecules which adapt or carry out the activation of a KAR can be for example chosen from the molecules with an SH2 or PTB domain. These can be in soluble recombinant form.

The stage of bringing into contact can be, for example, carried out by coupling the candidate molecules, obtained in soluble recombinant form, likely to be molecules which adapt or carry out the activation of a KAR, to balls allowing the measurement of radioactivity such as balls of scintillating liquid, and by passing polypeptides according to the invention (or fragments or homologues of such polypeptides) in tritiated form over said balls. Those candidate molecules for which a binding to said polypeptides, fragments, or homologues is observed by measuring the radioactivity (cpm) are then selected.

The stage of bringing into contact can also be carried out by immobilization of polypeptides according to the invention (or fragments or homologues of such polypeptides) on microsupports allowing the measurement of the plasmon resonance such as BIAcore microsupports (Pharmacia) (cf. for example Olcese et al., 1996, The Journal of Immunology 156:4531-4534; Vely et al., Immunology Letters 1996, vol. 54, p145-150), or by immobilization of phosphorylated and biotinylated polypeptides according to the invention on streptavidine balls (Vély et al. Eur. J. Immunol. 1997, 27: 1994-2000; Le Dréan et al. Eur. J. Immunol. 1998, 28: 264-276), and by passing, over said microsupports, candidate molecules likely to be molecules which adapt or carry out the activation of a KAR. Those candidate molecules for which a binding to said polypeptides, fragments, or homologues is observed by measuring the plasmon resonance (Resonance Unit) are then selected.

This method of identifying the molecules which adapt or carry out the activation of a KAR, whatever its implementation method, can also be used as a reference for the implementation of the method for identifying molecules capable of modulating a cell activity resulting from the activation of a KAR according to the invention.

This method of identifying molecules capable of modulating a cell activity resulting from the activation of a KAR, according to the invention, comprises the following stages:
   i. bringing the candidate molecules into contact with molecules which adapt or carry out the activation of a KAR as obtained by the method according to the invention described above and with polypeptides according to the invention (or with fragments or homologues of such polypeptides), and
   ii. selection of those candidate molecules which have an effect on the binding between said polypeptides (or said fragments or homologues of polypeptides) and said molecules which adapt or carry out the activation, as observed in the absence of said candidate molecules.

The candidate molecules likely to modulate a cell activity resulting from a KAR can be chosen from banks of natural or synthetic compounds, in particular from chemical or combinatory banks. Said candidate molecules can be of protein nature (for example, derivatives or fragments of anti-idiotype antibodies such as the antibodies according to the invention, derivatives or fragments of catalytic antibodies), of carbonated, lipidic or nucleic nature.

The bringing-into-contact stage of the method for identifying molecules capable of modulating a cell activity resulting from the activation of a KAR, according to the invention, can be, for example, carried out by incubation of said candidate molecules with polypeptides according to the invention (or with fragments or homologues of such polypeptides) and with molecules which adapt or carry out the activation of a KAR, as obtained by the method according to the invention, under conditions allowing measurement of the degree of binding between said polypeptides and said molecules which adapt or carry out the activation of a KAR, for example, based on a chemical property of said molecules which adapt or carry out the activation in a non-bound state, such as an enzymatic property, phosphorylation or self-phosphorylation property.

The bringing-into-contact stage of the method for identifying molecules capable of modulating a cell activity resulting from the activation of a KAR, according to the invention, can also be carried out by implementing techniques of the scintillating liquid balls type and tritiated polypeptides or polypeptides of microsupport type and measurement of the plasmon resonance, as described above, by measuring the radioactivity or, respectively, the plasmon resonance, resulting from the binding between said polypeptides and said molecules which adapt or carry out the activation, in the absence and in the presence of candidate molecules. Those candidate molecules which either increase or decrease in a statistically significant manner the control degree of binding measured between said polypeptides and said molecules which adapt or carry out the activation in the absence of said candidate molecules are then selected.

The molecules capable of modulating the activation of a KAR, as identified by the method according to the invention, can be modified chemically in order to render them non-hydrolysable under biological conditions, and/or so that they can cross a double lipidic cell layer.

The molecules capable of modulating the activation of a KAR, according to the invention, advantageously act by modifying the interaction between said KARAPs and their cellular effectors or adaptors.

Said molecules capable of modulating a cell activity resulting from the activation of a KAR, according to the present invention, can then be applied to a cell cultivated in vitro, such as a lymphocyte cell, of which the KAR activity has been stimulated, for example, by bringing it into contact with a ligand. This application is achieved by penetration inside said cell, for example, by electroporation or by chemical modification allowing a double lipidic layer to be crossed.

The present invention is illustrated by the following examples which should be in no event be considered as limitative.

Figure 3A:
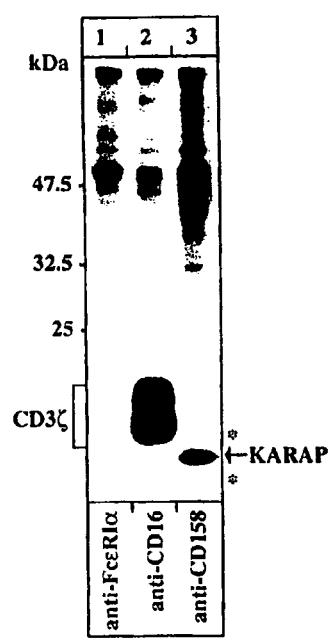
Figure 4:
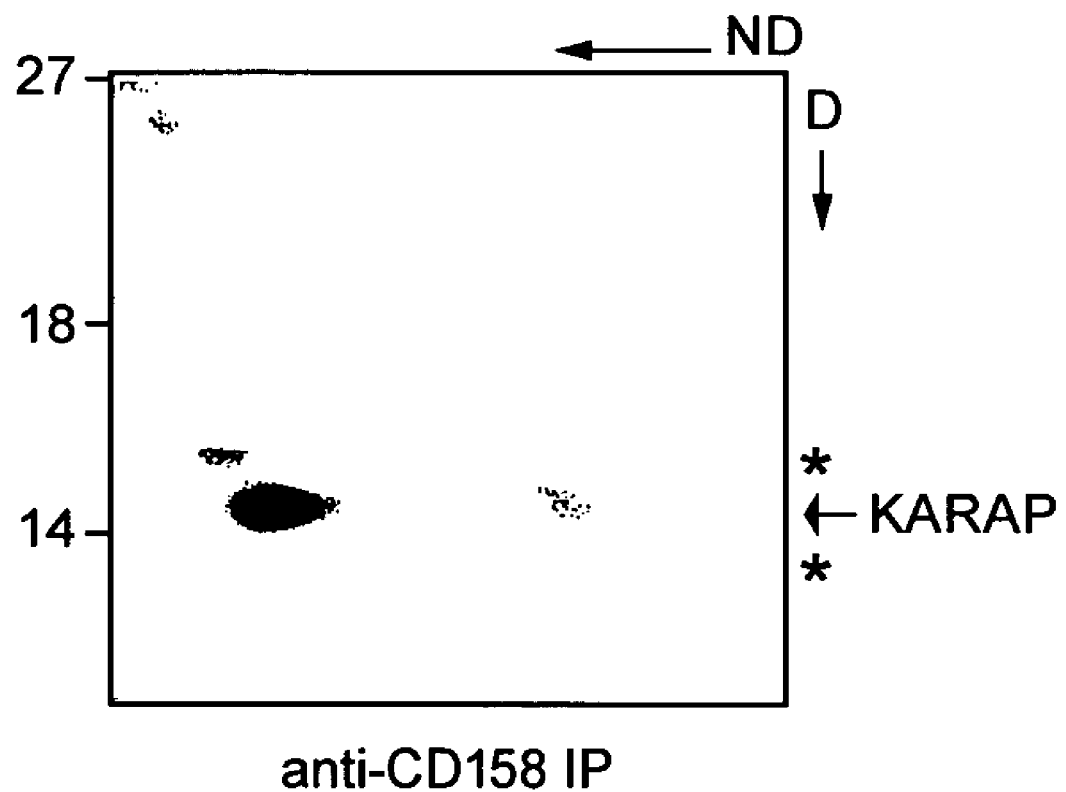
Figure 5:
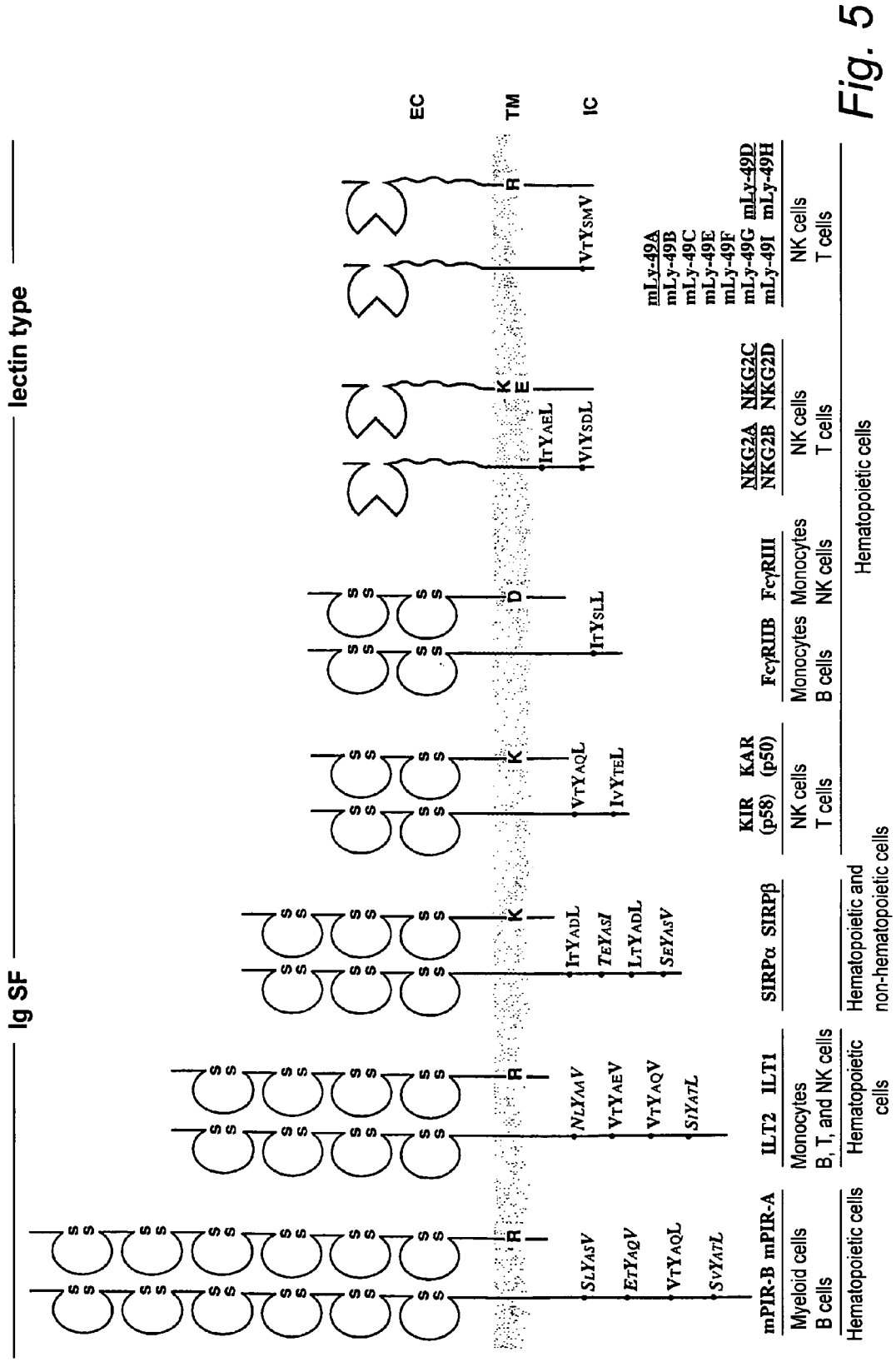
Figure 20:
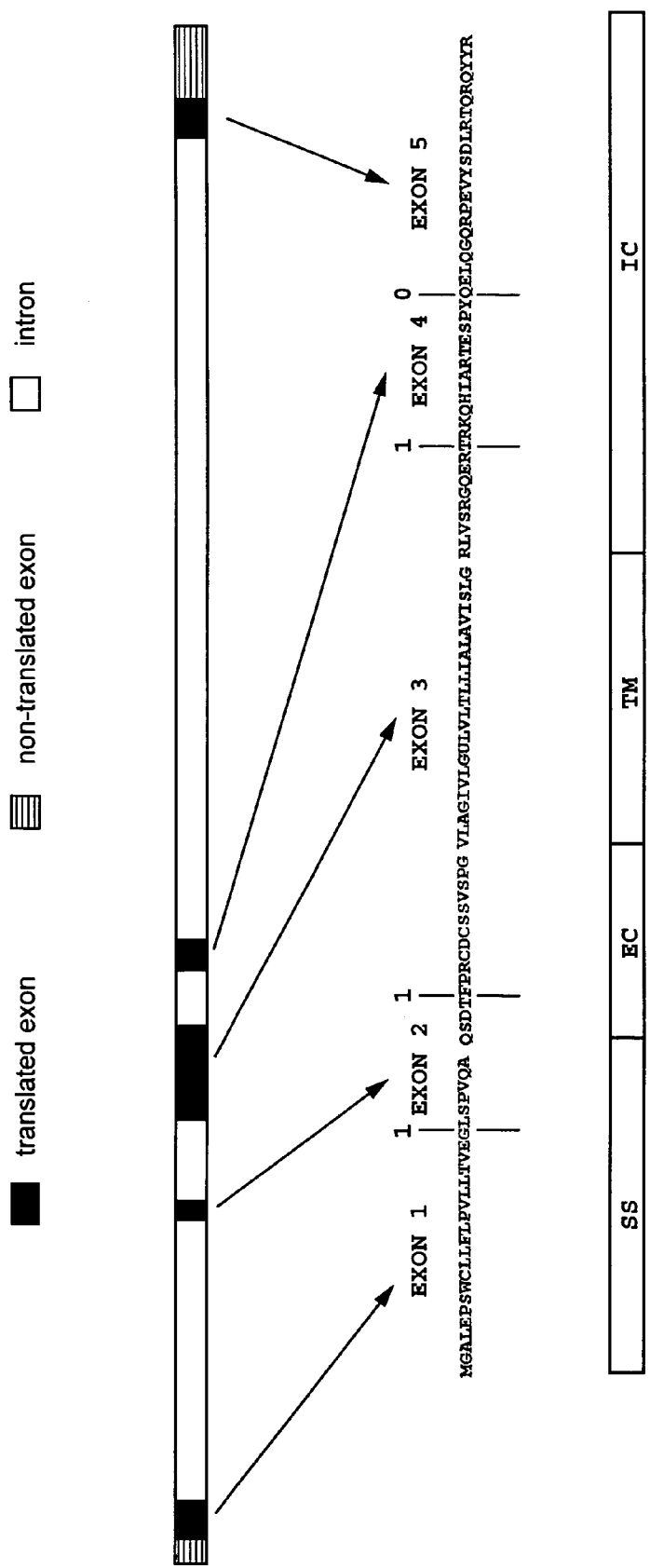
Figure 22:
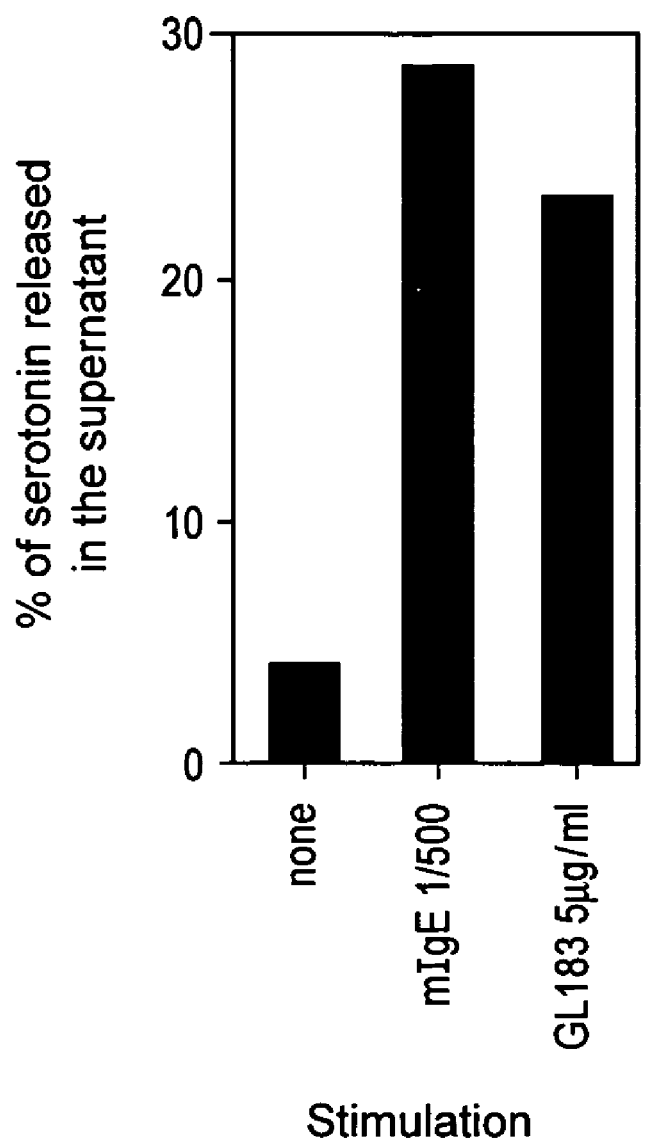
Figure 23:
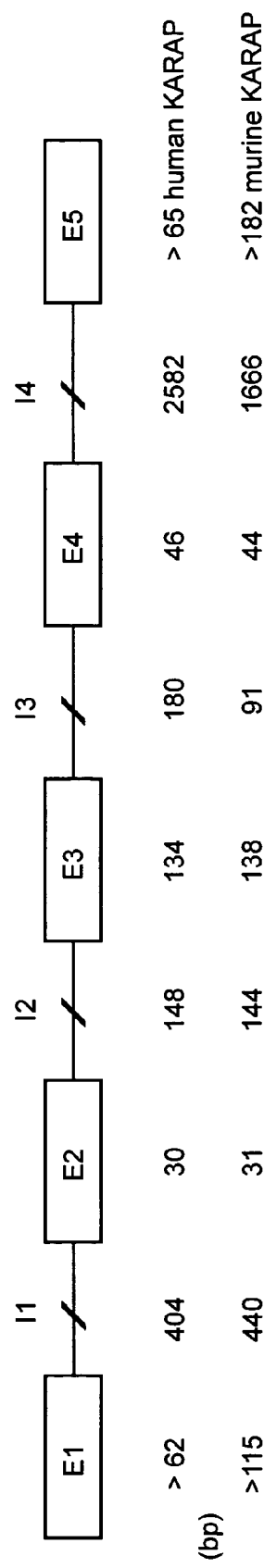

Reference is made to the 23 following figures:

FIG. 1 shows in A, an analysis by flow cytometer (FACScan, registered trade mark of Becton-Dickinson) in indirect immunofluorescence of cells cultivated on IL-2 (interleukin 2) and from patients suffering from LDGL (lymphoproliferative disease of the granular lymphocytes) designated R.P., D.F. and MAL., and in B, the results of a re-directed cytotoxicity test with different monoclonal antibodies, carried out on NK cells cultivated on IL-2 from different donors;

FIG. 2 shows:

in A, an SDS-PAGE analysis (resolution of proteins by electrophoresis on gel and sodium dodecyl sulphate) carried out from NK cells of donor R.P. (p50.1$^+$) radiomarked with $^{125}$I and immunoprecipitated using the monoclonal anti-CD158 EB6 antibody, before and after exhaustion of FceRIγ and of CD3ζ using anti-CD3ζ anti-FceRIγ antibodies, in B, an SDS-PAGE analysis with an anti-CD3ζ antibodies probe of full lysates of D.F. cells or of immunoprecipitates of such lysates;

FIG. 3 shows:

in A, SDS-PAGE analysis of the phosphorylated proteins originating from in vitro kinase tests to which immunoprecipitates of lysates of NK MAL. cells have been subjected, in B, the same type of SDS-PAGE analysis as in FIG. 3A but carried out from RBL-2H3 p50.2$^+$ cells, in C, an analysis by thin-layer electrophoresis (TLE) of the phosphorylated amino acids of the KARAPs and CD3ζ bands excised after in vitro kinase tests carried out on anti-CD158 and anti-CD16 immunoprecipitates, respectively, of NK R.P. cells, FIG. 4 shows a 2-dimensional SDS-PAGE analysis under non-denaturing/denaturing conditions of anti-CD158 immunoprecipitates of lysates of cells NK R.P. having undergone a kinase test, and FIG. 5 shows the activatory or non-inhibitory receptors of the immunoglobulins superfamily (IgSF) or of lectin type, and their inhibitory counterparts, FIG. 6 shows the schematic structure of KIR (p58) and KAR (p50) receptors, FIG. 7 shows the cDNA sequence of a mouse KARAP polypeptide according to the invention (SEQ ID no. 1), FIG. 8 shows the nucleotide sequence (residues 138 to 398 of SEQ ID NO: 1) (comprised between the excluded leader sequence and the stop codon) and the amino acids sequence of a KARAP polypeptide according to the invention (mature protein, SEQ ID no. 2), and FIG. 9 shows the alignment of the ITAMs (SEQ ID NOS 32-41, respectively in order of appearance) and of the ITAM of a KARAP polypeptide (SEQ ID NO: 42) according to the invention, FIGS. 10A, 11A, 12A, 13A and 14A respectively illustrate the cDNA sequences of the EST's AA242315, AA734769, W88159, AA098506 and W41142 (SEQ ID no. 6 to SEQ ID no. 10), FIGS. 10B, 11B, 12B, 13B and 14B respectively illustrate the protein sequences of the EST's AA242315, AA734769, W88159, AA098506 and W41142 (SEQ ID no. 11 to SEQ ID no. 15), FIG. 15 shows the alignment of the cDNA sequences of the EST's AA242315 (SEQ ID NO:6), AA734769 (SEQ ID NO:7), W88159 (SEQ ID NO:8), AA098506 (SEQ ID NO:9) and W41142 (SEQ ID NO:6), and the resulting consensus sequence (SEQ ID no. 16; KARAP consensus cDNA of mouse C57Bl/16), FIG. 16 represents the alignment of the protein sequences of the EST's AA242315 (SEQ ID NO:11), AA734769 (SEQ ID NO:12), W88159 (SEQ ID NO:13), AA098506 (SEQ ID NO:14) and W41142 (SEQ ID NO:15), and the resulting consensus sequence (SEQ ID no. 17; KARAP consensus protein of mouse C57Bl/6), FIG. 17 shows the sequence of the KARAP gene of a mouse of line 129 (SEQ ID no. 18; 2838 pb), FIG. 18 shows the genomic organization of the KARAP of a mouse of line 129, FIG. 19 shows the cDNA sequence of the KARAP of a mouse of line 129 (SEQ ID no. 27) and the corresponding protein sequence (SEQ ID no. 28), FIG. 20 represents from top to bottom the genomic organization of the KARAP gene of a mouse of line 129, the corresponding protein sequence (SEQ ID NO:44), and the nature of the different regions of this protein, FIG. 21 shows the cDNA of the human KARAP (SEQ ID no. 31), FIG. 22 shows the percentage of serotonin salted out in the supernatant by the doubly transfected p50/human KARAP RBL-2H3 cells, and stimulated by the antibody indicated on the abscissa (on the left: no antibodies; in the centre: mouse IgE: mIgE 1/500; on the right: GL183 5 μg/ml), FIG. 23 illustrates the homology between the organization of the human KARAP gene and that of the murine KARAP gene.

EXAMPLE 1

1. Materials and Methods

Monoclonal Antibodies (mAbs) and Reagents

The following monoclonal antibodies were used:
anti-CD3, anti-CD16 and anti-CD56 antibodies of isotype IgG1, such as JT3A (Coulter Immunotech reference 0178), KD1 (Coulter Immunotech reference 0813) and TA181.H12 (Coulter Immunotech reference 1844), respectively, anti-CD3ζ antibodies such as TIA-2 (Coulter Immunotech 66045P2), anti-CD158 antibodies, namely anti-p58.1 antibodies such as EB6 (Coulter Immunotech reference 1847), anti-p58.2 antibodies such as GL183 (Coulter Immunotech reference 1846) and anti-p50.3 antibodies such as PAX250 described in Bottino et al. (*Eur. J. Immunol.*, 1996, 26, 1816), an anti-FcεRIγ rabbit antiserum such as antiserum 666 described in Jouvin M. H. et al., 1994, *J. Biol. Chem.*, 269, 5918-5925, an anti-FcεRIα rabbit antiserum such as antiserum BC4 described in Bociano L. K. et al., 1986, *J. Biol. Biochem.*, 261, 11823-11831, an anti-mouse goat antiserum conjugated with horseradish peroxidase (Sigma A-2304) and an anti-rabbit goat antiserum conjugated with horseradish peroxidase (Sigma A-0545), an anti-mouse goat immunoglobulin conjugated with fluorescein isothiocyanate (Coulter Immunotech 0819 F(ab')$_2$) and GL183-phycoerythrin (GL183-PE) monoclonal antibodies (Coulter Immunotech 2278), EB6-phycoerythrin (EB6-PE) monoclonal antibodies (Coulter Immunotech 2277) and an anti-mouse-phycoerythrin (anti-mouse-PE) goat immunoglobulin (Coulter Immunotech 0855 F(ab')$_2$).

The lysis buffer contained Tris-HCl 25 mM pH 7.5; NaCl 150 mM; digitonin 1%; sodium orthovanadate 100 μM; NaF 10 mM; aprotinin 2 μg/ml; leupeptin 2 μg/ml; all these products were purchased from Sigma (St Louis, Mo., USA).

The kinase buffer contained Hepes 20 mM pH 7.2; NaCl 100 mM; MnCl$_2$ 5 mM; MgCl$_2$ 5 mM; $^{32}$γ ATP 10 μCi=370 kBq (Amersham, Buckinghamshire, UK).

The thin layer electrophoresis (TLE) buffer contained 10% glacial acetic acid and 1% pyridine in water; pH 3.5.

Cells

Human NK Cells from LDGL Patients, or LDGL Cells

The human NK cells were obtained from patients suffering from lymphoproliferative disease of granular lymphocytes (LDGL) of the CD56$^+$, CD16$^+$, CD3$^+$ NK cell line. Peripheral blood lymphocytes (PBL) were isolated from blood samples of patients suffering from LDGL by Ficoll/Hypaque gradient centrifugation. These LDGL cells were then cultivated at 37° C. at a concentration of $10^6$ cells per ml on RPMI-1640 medium containing 10 μg/ml of penicillin-streptomycin and 10% of foetal calf serum, in the presence of allogenic irradiated nurse cells and 100 U/ml of rIL-2.

Preparation of RTIIB.p50.2$^+$ Transfected Cells

Transfectants of RBL-2H3 cells (American Type Culture Collection) expressing p50.2 KARs (RTIIB.p50.2$^+$ cells) were prepared as described in Bléry et al., 1997, *J. Biol. Chem.*, 272, 8989-8996. FIG. 6 schematically shows the structure of p58 KIRs (immunoglobulin-type inhibitory human receptors) and p50 KARs (non-inhibitory counterpart of p58 KIRs).

In brief, the RTIIB cells used are the cells conventionally described as being RBL-2H3 cells transfected so as to express the murine FcγRIIb2 receptor and the CD25/CD3 chimeric molecule comprising the complete ectomembrane and transmembrane domains of human CD25 bound to the complete intracytoplasmic domain of murine CD3.

These RTIIB cells were also transfected, by electroporation, with 183.Act2 cDNA (coding for p50.283) carried on expression vector RSV-5gpt.

Stable RTIIB.p50.2$^+$ transfected cells were established by culture in the presence of xanthine (250 μg/l), hypoxanthine (13.6 μg/l) and mycophenolic acid (2 μg/l).

Cytolytic Test

The cytolytic activity of LDGL cells cultivated on IL-2 was measured relative to the P815 murine cell line (American Type Culture Collection) in the absence or presence of anti-CD16, anti-CD158 and anti-CD56 mAbs.

In brief, $5 \times 10^3$ target cells labelled with $^{51}$Cr were added to serial dilutions of effector cells in the presence of 50 μl of hybridoma supernatant monoclonal antibody at the start of the standard $^{51}$Cr release test lasting 4 hours (Vivier E. et al., 1991, *J. Immunol.*, 146, 206).

Radioiodination

The cells ($10$-$50 \times 10^6$) were fixed with 0.5% formaldehyde in PBS (sodium phosphate buffer) and then permeabilized for 5 minutes with digitonin at a concentration of 30 μg/ml in PBS, prior to iodination catalyzed by lactoperoxidase ($^{125}$I, NEN-Dupont, Wilmington, Del., USA), as described by Anderson P. et al., 1989, *J. Immunol.*, 143, 1899.

The cells were lyzed for 30 minutes at 4° C. in a digitonin lysis buffer. The prepurified postnuclear supernatants were then immunoprecipitated with specific antibodies covering S4B-Sepharose beads (Pharmacia, Piscataway, N.J., USA) (Vivier E. et al., 1991, *J. Immunol.*, 146, 206). The immunoprecipitates were analyzed by SDS-PAGE (protein resolution by electrophoresis on gel and sodium dodecylsulfate) and autoradiography.

In Vitro Kinase Test

The cells ($10 \times 10^6$ per sample) were lyzed in 1 ml of lysis buffer (cf. reagents). The prepurified postnuclear supernatants were immunoprecipitated for 2 to 3 hours using monoclonal antibodies covalently bonded to a Sepharose 4B activated by CnBr (Pharmacia). The immune complexes were washed three times in lysis buffer; 40 μl of kinase buffer (cf. reagents) were then added to the immunoprecipitates over 10 minutes at 37° C. The kinase reaction was stopped by the addition of SDS-sample reducing buffer. The samples were brought to the boil prior to analysis by SDS-PAGE and autoradiography. In some experiments, the samples were analyzed by two-dimensional non-denaturing/denaturing diagonal SDS-PAGE.

Analysis of the Phosphorylation of the KARAPs

After the in vitro kinase test and the separation by SDS-PAGE, the phosphorylated proteins were cut out of the dried gels and eluted using a Centrilutor (Amicon) or a 0.1% solution of SDS (sodium dodecylsulfate) in PBS (sodium phosphate buffer). The eluted proteins were precipitated in 20% trichloroacetic acid at 4° C. for 2 hours, prior to incubation in 200 μl of 5.7 M HCl at 110° C. for 90 minutes. The individual amino acids were then dried and resuspended in 5 μl of TLE buffer (cf. reagents) containing 5 μg each of unlabelled phosphotyrosine, phosphothreonine and phosphoserine (Sigma) as standard references. The samples were deposited on plates of cellulose (100 μm DC cellulose) and caused to migrate at 1500 V for 45 minutes at 4° C. on a Multiphor II (Pharmacia). Standard references were developed with 1% ninhydrin in acetone and the $^{32}$P-labelled amino acids were identified by autoradiography.

Analysis by Immunotransfer

The immunoprecipitates were resolved by SDS-PAGE, transferred to nitrocellulose filters and compared with anti-CD3ζ or anti-FcεRIγ antibody probes diluted in PBS solution containing 5% of skimmed dried milk. The immunotransfers were revealed using an anti-mouse or anti-rabbit goat antiserum conjugated with horseradish peroxidase (Sigma references A-2304 and A-0545 respectively) and the ECL detection system marketed by Amersham (RPN 2209).

2. Results

Surface Phenotype

The surface phenotype of the NK cells taken from LDGL patients and cultivated on IL-2 (interleukin-2) was analyzed by FACScan (screening of fluorescence-activated cells) using the indirect immunofluorescence method.

The results of the study relating to three of these patients, hereafter called R.P., D.F. and MAL., are reported below.

Said results are illustrated in FIG. 1A, which shows an indirect immunofluorescence FACScan analysis of R.P., D.F. or MAL. LDGL (lymphoproliferative disease of granular lymphocytes) cells cultivated on IL-2. An anti-mouse goat immunoglobulin conjugated with fluorescein isothiocyanate was used as the reagent in the second step. For each type of LDGL cells (R.P. LDGL cells for the analyses shown in the top horizontal band, D.F. LDGL cells for those of the middle horizontal band, MAL. LDGL cells for those of the bottom horizontal band) and for each treatment undergone (control treatment C for the graphs shown on the left or treatment with the indicated monoclonal antibody, i.e., from left to right, anti-CD3, anti-CD16, anti-CD158 EB6, anti-CD158 GL183, anti-CD158 PAX250), the fluorescence intensities are plotted on the abscissa and the relative number of cells is plotted on the ordinate.

It can be observed that:
the R.P., D.F. and MAL. NK cells are all CD3$^+$ and CD16$^+$;
the R.P. NK cells are p50.1$^+$, p50.2$^+$, p50.3$^+$: they are recognized by the anti-CD158 monoclonal antibody EB6 and are not recognized by the anti-CD158 monoclonal antibodies GL183 and PAX250;
the D.F. NK cells are p50.1$^+$, p50.2$^+$, p50.3$^+$: they are recognized by the anti-CD158 monoclonal antibody GL183 and are not recognized by the anti-CD158 monoclonal antibodies EB6 and PAX250; and
the MAL. NK cells are p50.1$^+$, p50.2$^+$, p50.3$^+$: they are recognized by the anti-CD158 monoclonal antibody PAX250 and are not recognized by the anti-CD158 monoclonal antibodies EB6 and GL183.

The three patients suffering from LDGL therefore showed a lymphoproliferation of NK cells which was recognized by anti-CD158 antibodies: anti-p58.1 KIR (EB6), anti-p58.2 KIR (GL183) and anti-p50.3 KAR (PAX250) respectively. Three groups of NK cells could thus be defined: R.P. LDGL cells, D.F. LDGL cells and MAL. LDGL cells.

Cytolytic Test

Redirected cytotoxicity tests using P815 as FcγR$^+$ target cells were carried out on the R.P. p50.1$^+$, D.F. p50.2$^+$ and MAL. p50.3$^+$ NK cells.

Figure 1B:
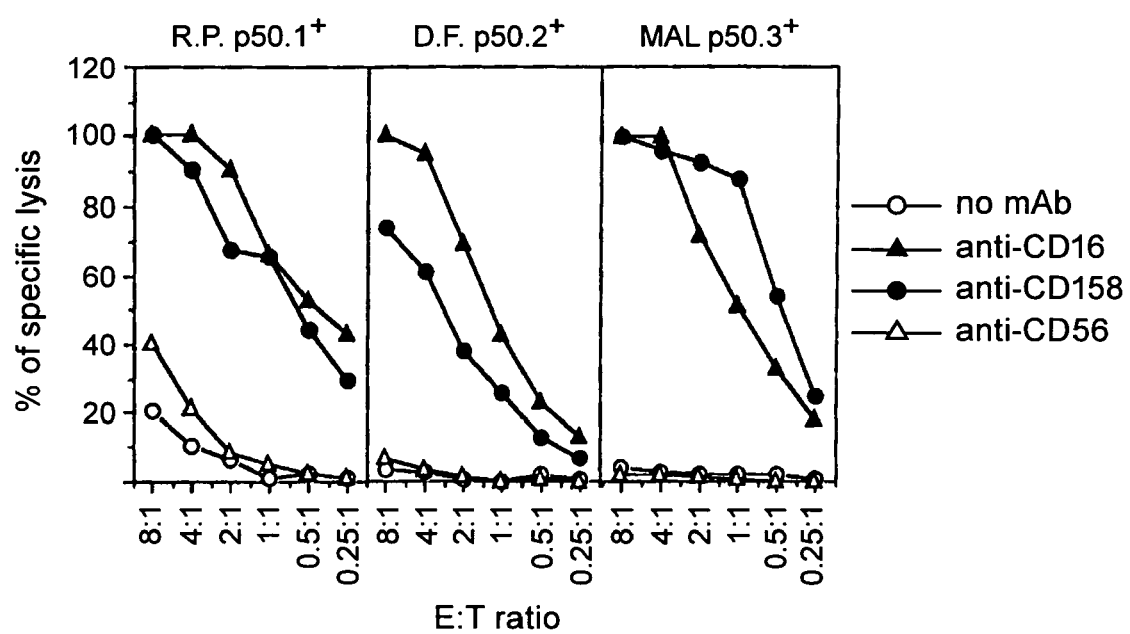

The results are illustrated in FIG. 1B, which shows a redirected cytotoxicity test with different monoclonal antibodies: NK cells taken from the indicated donors (R.P. p50.1$^+$ on the left, D.F. p50.2$^+$ in the centre or MAL. p50.3$^+$ on the right) and cultivated on IL-2 were used as effector cells. The test was carried out in the presence of: no antibody (white circles), anti-CD16 monoclonal antibody (black triangles), anti-CD56 monoclonal antibody (white triangles), anti-CD158 monoclonal antibody (EB6 for R.P., GL183 for D.F. and PAX250 for MAL.) (black circles). The ratios of effector cells to target cells (E:T ratio: 8:1; 4:1; 2:1; 1:1; 0.5:1; 0.25:1) are plotted on the abscissa and the percentage of specific lysis (scale from 0 to 120%) is plotted on the ordinate.

The redirected cytotoxicity tests indicate that, by contrast with what is observed when stimulating KIRs, the addition of anti-CD158 antibodies to the NK cells considerably increases the cytolysis of the P815 cells (FIG. 1B).

As controls, the anti-CD16 monoclonal antibodies increase the spontaneous cytolysis of the P815 cells in a manner similar to the anti-CD158 monoclonal antibodies, whereas an anti-CD56 monoclonal antibody matched to the isotype has no effect (FIG. 1B).

These NK cells therefore express KARs, the activatory isoform of KIRs, on their surface. These results were further confirmed by PCR (polymerase chain reaction) analyses with KIR/KAR cDNA reverse transcriptase.

Analysis of the Expressed KARs by Radioiodination and Immunotransfers: Identification of the KARAPs The KARs expressed on the NK cells taken from LDGL patients were analyzed by internal radioiodination followed by immunoprecipitation.

The results are illustrated in FIG. 2A, which shows an SDS-PAGE analysis on a 13% gel under denaturing conditions, carried out on NK cells (10×10$^6$ cells/lane) from the donor R.P. (p50.1$^+$) which have been radiolabelled with $^{125}$I, immunoprecipitated with the anti-CD158 monoclonal antibody EB6 (lane 1), then purified with anti-CD3ζ anti-FcεRIγ monoclonal antibodies (lanes 2 to 7) and finally re-immunoprecipitated with the anti-CD158 monoclonal antibody EB6 (lane 8).

The same profiles were obtained with the donors D.F. (p50.2$^+$) and MAL. (p50.3$^+$) (data not shown).

It can be seen that the immunoprecipitates of anti-CD158 antibodies prepared from lyzates of NK cells contain, in addition to the KARs observed at ≈50 kDa, a band of lower molecular weight migrating to about 12±1 kDa.

It was shown that KIRs associate with the polypeptides CD3ζ and FcεRIγ in human NK cells. Pre-exhaustion experiments using anti-CD3ζ and anti-FcεRIγ antibodies eliminated the possibility that the band at about 12 kDa associated with the KARs might be CD3ζ or FcεRIγ (FIG. 2A).

The group of proteins corresponding to this band at about 12±1 kDa was given the name KARAPs (KAR-associated proteins).

These results were confirmed by immunotransfer experiments, which revealed the absence of any reactive band in the presence of anti-CD3ζ antibodies in the immunoprecipitates of anti-CD158 mAbs prepared from NK lyzates.

These results, obtained in the presence of anti-CD3ζ antibodies, are illustrated in FIG. 2B, which shows an analysis of complete lyzates of D.F. cells, or immunoprecipitates of such lyzates, by SDS-PAGE resolution on a 15% gel under denaturing conditions and incubation of the nitrocellulose filters with an anti-CD3ζ monoclonal antibody probe (marker arrow on the right). The complete lyzates of D.F. cells (CCL) were deposited at the rate of 5×10$^6$ cells/lane in lane 1 and the immunoprecipitates of such lyzates were deposited at a rate of 15×10$^6$ cells/lane in lanes 2 to 4. The immunoprecipitations were carried out on lyzates of D.F. cells using the anti-FcεRIα monoclonal antibody BC4 in control lane 2, the anti-CD16 monoclonal antibody in lane 3 and the anti-CD158 monoclonal antibody GL183 in lane 4.

The same results were obtained for the R.P. and MAL. cells with anti-CD3ζ mAb.

The results obtained with anti-FcεRIγ mAb (data not shown) provided the same confirmation.

Analysis of the KARAPs by an In Vitro Kinase Test and Thin Layer Electrophoresis (TLE)

In vitro kinase tests carried out on the immunoprecipitates of anti-CD158 monoclonal antibodies revealed that the KARs associate with a predominant phosphoprotein of low molecular weight migrating to about 14±1 kDa in the NK cells.

The results are illustrated in FIG. 3A: lyzates prepared from MAL. NK cells were immunoprecipitated with the indicated antibody (anti-FcεRIα in lane 1, anti-CD16 in lane 2, anti-CD158 in lane 3) prior to in vitro kinase tests. The phosphorylated proteins were separated by SDS-PAGE on a 15% gel under denaturing conditions.

These results are consistent with the expected change of molecular weight for the phosphorylated form of the KARAP at 12 kDa, observed by internal iodination. Furthermore, the immunoprecipitates of anti-CD158 mAbs prepared from KAR$^+$ NK cells comprise two other phospho-KARAPs migrating to 16±1 kDa and 12±1 kDa respectively (indicated by an asterisk on either side of the KARAP arrow at 14 kDa in FIG. 3A).

Association of the KARs with a similar group of phosphorylated KARAPs was also observed with a panel of clones of KAR$^+$ NK cells and was absent from KIR$^+$ NK clones. It was seen that the relative intensity of the phospho-KARAPs at 16, 14 and 12 kDa can vary according to the origin of the NK cells.

Analysis of the phosphorylated amino acids revealed that the major KARAP at 14 kDa is principally phosphorylated on the tyrosine residues.

Figure 3B:
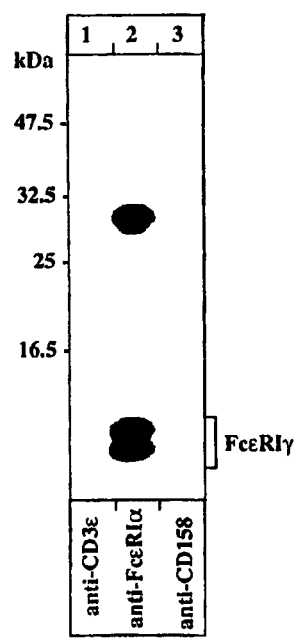
Figure 3C:
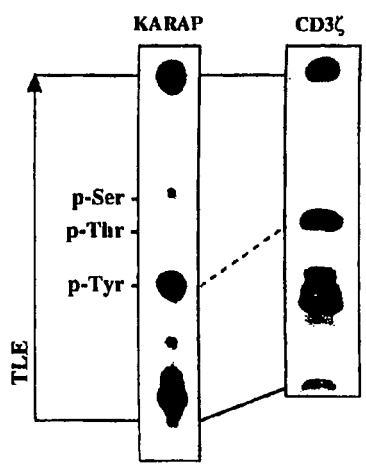

The results are illustrated in FIG. 3C: the bands of KARAPs (on the left) and CD3ζ (on the right) were cut out after the in vitro kinase test and subjected to an analysis of the phosphorylated amino acids by thin layer electrophoresis. In this experiment, the KARAP and CD3ζ bands were isolated from immunoprecipitates of monoclonal antibodies, respectively anti-CD158 and anti-CD16 monoclonal antibodies, prepared from lyzates of R.P. NK cells.

Nevertheless, phosphorylation on the serine residues but not on the threonine residues can also be detected. As a control, analysis of the phosphorylated amino acids confirmed the phosphorylation of CD3ζ on the tyrosine residue only.

KARAPs and Transduction of the Activatory Signal (KAR$^+$ Transfectants)

By contrast with the p58.2 KIRs, the expression of p50.2 KAR in the transfectants of the RBL-2H3 non-lymphoid cell line does not lead to reconstitution of the activatory function of the p50.2 KARs. In fact, the stimulation of transfectants of p50.2$^+$ RBL-2H3 cells induced by anti-CD158 antibodies does not lead to any detectable mobilization of the intracytoplasmic Ca$^{2+}$ or to any detectable release of serotonin.

Remarkably, in vitro kinase tests carried out on the immunoprecipitates of anti-CD158 monoclonal antibodies prepared from transfectants of p50.2$^+$ RBL-2H3 cells did not include any detectable KARAP.

The results are illustrated in FIG. 3B: lyzates prepared from p50.2$^+$ RBL-2H3 cells were immunoprecipitated with the indicated antibody (anti-CD3ε in lane 1, anti-FcεRIα in lane 2, anti-CD158 in lane 3) prior to in vitro kinase tests. The phosphorylated proteins were separated by SDS-PAGE on a 15% gel under denaturing conditions.

The lack of association of the KARs with the KARAPs in the transfectants of p50.2$^+$ RBL-2H3 cells was also confirmed by internal iodination (data not shown).

The KARAPs therefore associate selectively with the KARs and the absence of association of the KARs with the KARAPs is correlated with the inability of the KARs to transduce any detectable activatory signal.

Association of KARs with KARAPs (Diagonal Gel)

Finally, analysis of the immunoprecipitates of anti-CD158 monoclonal antibodies on a diagonal two-dimensional gel revealed that the phospho-KARAPs at about 16, 14 and 12 kDa decrease along the diagonal gel.

The results are illustrated in FIG. 4: immunoprecipitates (IPs) of anti-CD158 monoclonal antibodies prepared from lyzates of R.P. NK cells were subjected to an in vitro kinase test prior to analysis by SDS-PAGE on a two-dimensional 13% gel under non-denaturing (horizontal direction)/denaturing (vertical direction) conditions.

These results thus indicate that the KARs are associated in the NK cells with a complex of KARAP dimers bonded by a disulfide linkage.

3. Discussion

KARs, which are autonomous activatory receptors, especially for class I MHC molecules, or coreceptors for the TCR (T cell receptor) or the cFR (immunoglobulin constant fragment receptor), represent a new way of activating the NK and T cells.

The inventors have shown that KARs are in fact assembled in the NK cells in the form of a multimeric complex involving KARAPs associated to form dimers bonded by a disulfide linkage.

Although analysis by radioiodination revealed one KARAP at about 12±1 kDa, analysis by the kinase test revealed three phospho-KARAPs at about 16, 14 and 12±1 kDa.

The correlation between the association of the KARs with the KARAPs and the activatory function of the KARs suggests that the KARAPs act as transducing subunits of the multimeric KAR complex.

However, the absence of association of the KARs with the KARAPs, as observed for the transfectants of RBL-2H3 cells, does not prevent expression of the receptor on the cell surface, contrary to what was observed in the case of the multimeric activatory receptors for antigens or antibodies including polypeptides with an ITAM (immunoreceptor activatory moiety based on tyrosine residue(s)).

Other activatory or at least non-inhibitory receptors of the immunoglobulin superfamily possess striking similarities to the p50 KARs (immunoglobulin-type human KARs): NKG2C/D lectin-type human KARs, pirA and gp49A immunoglobulin-type murine KARs, Ly49D and Ly49H lectin-type murine KARs, but also human activatory receptors of the LIR/MIR/ILT family, such as ILT1.

These similarities are illustrated in FIG. 5, which shows the activatory or non-inhibitory receptors of the immunoglobulin superfamily (IgSF) or of the lectin type, and their inhibitory counterparts. Indicated underneath the name of each pair of receptors (from left to right: mPIR-B-mPIR-A, ILT2-ILT1, SIRPα-SIRPβ, KIR-KAR, FcγRIIB-FcγRIII, NKG2A/B-NKG2C/D, mLy49A/B/C/E/F/G/I-mLy49D/H) are the cells which express them naturally. The activatory or non-inhibitory receptors possess neither an ITIM (immunoreceptor inhibitory moiety based on tyrosine residue(s)) nor an ITAM (immunoreceptor activatory moiety based on tyrosine residue(s)), but do possess a charged amino acid residue in their transmembrane domain (TM) (R=arginine, K=lysine, D=aspartic acid, E=glutamic acid). The inhibitory counterparts (left item of each pair) contain an ITIM in their intracytoplasmic part (IC). In the extracytoplasmic part (EC), each activatory or non-inhibitory receptor has a high homology with its inhibitory counterpart.

EXAMPLE 2

Biochemical characterization of the KARAP molecules (cf. Example 1 above) enabled us to specify the main identification criteria for the KARAP polypeptides, which were particularly as follows:
  polypeptides containing an extracytoplasmic cysteine amino acid allowing the formation of disulfide bridges (cf. FIG. 4),
  polypeptides with an apparent molecular weight of between about 12 and 16 kDa, and
  polypeptides having at least one phosphorylatable tyrosine amino acid (cf. FIG. 3C).

Given the strong similarities existing between the KARAP molecules identified at 12, 14 and 16 kDa, we assumed that these three molecular forms represented different degrees of phosphorylation of the same KARAP polypeptide, whose molecular weight could not exceed 12 kDa.

Furthermore, a major characteristic of KARAPs lies in their selective association with KARs and not with KIRs. Given that, in contrast to KIRs, KARs possess a transmembrane charged amino acid (lysine: K) and that this particular feature is also the basis of the association of the ITAM polypeptides present in the complexes CD3/TCR, BCR, FcεRI and FcγRIIIA (CD16), we orientated our strategy for identification of the KARAP gene by considering that KARAP is a new member of the family of the ITAM transmembrane polypeptides. In fact, the latter share the same characteristics with KARAP:
  polypeptides containing an extracytoplasmic cysteine amino acid (C) allowing the formation of disulfide bridges,
  polypeptides with a low molecular weight not exceeding 25 kDa,
  polypeptides having at least one phosphorylatable tyrosine amino acid included in an ITAM: YxxL/Ix$_{6-8}$YxxL/I, and
  presence of a transmembrane charged amino acid.

We thus developed a biological data processing strategy for identifying a gene from the public cDNA libraries available in the EST, GENBANK, SWISSPROT and EMBL forms. We used 2 different approaches:
  1/We translated all the ESTs according to the 6 reading frames, singling out only the peptides which had between 50 and 200 amino acids (envisaged molecular weight of between 5.5 and 22 kDa). We applied several selection criteria to this sub-base:
    Existence of a predicted transmembrane region of at least 10 amino acids, starting with amino acid 30, by Argos' method (Rao & Argos, 1986, Biochem. Biophys. Acta, 869, 197-214). In fact, by homology with the ITAM polypeptides such as CD3ζ and FCεRIγ, the major part of the KARAP sequence is predicted as being intracytoplasmic.
    Search for an ITAM (Y-x-x-[IL]-x(6,8)-Y-x-x[IL]) in the C-terminal position of the transmembrane zone.
    Presence of a charged amino acid (R, K, D, E) in the transmembrane region.
    Presence of a cysteine amino acid (C) in the C-terminal position of the transmembrane zone.
  2/We searched for the EST entries (analysis also performed with EMBL, GENBANK and SWISSPROT) which had sequence similarities to the entry CD3Z_HUMAN. The program used was TBLASTN (version 1.4.11; Altschul, Stephen F., Warren Gish, Webb Miller, Eugene W. Myers and David J. Lipman, 1990, J. Mol. Biol., 215, 403-10) or TBLASTN (version 2.0.3; Altschul, Stephen F., Thomas L. Madden, Alejandro A. Schäffer, Jinghui Zhang, Zheng Zhang, Webb Miller and David J. Lipman, 1997, Nucleic Acids Res., 25, 3389-3402). To these similar entries we then applied the selection criteria used in the first approach.

By combining these two biological data processing approaches and after having successively determined the leader, transmembrane, intracytoplasmic and extracytoplasmic regions of the candidate molecules with the aid of hydrophobicity profiles (Genworks and DNA Strider programs), we obtained a large number of sequences potentially corresponding to that of KARAP. Among these sequences, the one corresponding to accession number AA242315 in Genbank appeared to us to be the sequence of the murine KARAP gene (SEQ ID no. 1, C57Bl/6 murine cDNA). FIG. 7 shows the DNA sequence (SEQ ID no. 1, cDNA) of a KARAP polypeptide according to the invention; this sequence corresponds to the sequence of the murine KARAP gene. In fact, translation of the nucleotide sequence gives an open reading frame of 396 nucleotides (SEQ ID no. 2). This result is illustrated in FIG. 8, which shows that part of the nucleotide sequence of the KARAP gene (SEQ ID no. 1) which is between the leader sequence (excluded) and the stop codon, and which also shows, underneath this nucleotide sequence, the corresponding amino acid sequence (1-letter code) (SEQ ID no. 2, 3-letter code), i.e. the amino acid sequence of the mature murine KARAP according to the invention (SEQ ID no. 2). Standard analysis of this sequence predicts a mature protein of 87 amino acids (molecular weight of 9.6 kDa), an extracytoplasmic part of 16 amino acids ($Q_1$-$G_{16}$), a transmembrane part of 24 amino acids ($V_{17}$-$G_{40}$) and an intracytoplasmic part of 47 amino acids ($R_{41}$-$R_{87}$. According to our search strategy, the extracytoplasmic part comprises at least one cysteine amino acid (in fact two, $C_8$ and $C_{10}$), a transmembrane amino acid ($D_{25}$) and an intracytoplasmic ITAM ($Y_{65}$QELQGQRHEVY$_{76}$SDL). FIG. 9 (SEQ ID NO:42) illustrates the comparisons which can be made by aligning sequences between the ITAM polypeptides described previously and the polypeptide according to the invention possessing one (or more) ITAMs, and indicates the resulting consensus ITAM sequence: FIG. 9 shows the alignment of the ITAMs of ITAM polypeptides (six CD3, one Igα, one Igβ, FcεRIγ and FcεRIβ) and an ITAM of the murine KARAP polypeptide (SEQ ID no. 2) identified above according to the invention (labelled "KARAP" in said FIG. 9). On the basis of this comparison with the ITAMs described previously (FIG. 9), we were able to envisage the association of the phosphorylated KARAPs with tyrosine kinase proteins containing SH2 groups in tandem (proteins such as ZAP-70 and p72Syk). The association of KARAPs with recombinant fusion proteins corresponding to the SH2 groups of ZAP-70 (preparation described in: Olcese L., Lang P., Vély F., Cambiaggi A., Marguet D., Bléry M., Hippen K. L., Biassoni R., Moretta A., Moretta L., Cambier J. C., Vivier E., 1996, J. Immunol., 156, 4531-4534) was verified in vitro: these experiments were carried out as described in FIG. 3A, lane 3, but the cell lyzates were adsorbed by the recombinant fusion protein corresponding to the SH2 groups of ZAP-70 instead of the anti-CD158 antibody. Thus KARAP is a novel ITAM transmembrane molecule which associates with KARs and which, in a phosphorylated tyrosine form, associates with ZAP-70. KARAP is therefore a novel transducing element of T and NK lymphocytes. It is possible that KARAP or KARAP analogues also associate with the activatory isoforms of ITIM receptors and serve in these multimolecular complexes as subunits for transducing the signals emitted when the receptor is taken up.

A particularly appropriate method of determining or checking that a candidate polypeptide of known sequence corresponds to a KARAP according to the invention consists in producing an antibody against a characteristic part of this candidate polypeptide (for example an intracytoplasmic region comprising at least one ITAM, or an extracytoplasmic region) and in verifying that this antibody recognizes, on a functional cell, for example a functional KAR+ cell, a target which is associated with the receptor for which the candidate polypeptide is assumed to be the KARAP (i.e., in the case of KAR+ cells, verifying that the antibody recognizes a target which is associated with a KAR).

This method of identifying KARAP polypeptides according to the invention thus consists in particular in:
producing a monoclonal or polyclonal antibody directed against this candidate polypeptide and in particular against a region of this candidate polypeptide which comprises at least one ITAM (for example, in the case of the murine KARAP identified above, an antibody directed against a region of the extracytoplasmic part (SEQ ID no. 3) or the intracytoplasmic part (SEQ ID no. 5) of SEQ ID no. 2),
bringing this antibody into contact with a lyzate of cells possessing, in a functional form, the activatory or non-inhibitory receptor for which the candidate polypeptide is assumed to constitute the KARAP, for example functional KAR+ cells such as NK or T cells, under mild conditions allowing binding reactions of the antigen-antibody type, and
identifying the candidate polypeptide as being a KARAP polypeptide according to the invention when the reaction products which may be formed contain a product whose apparent molecular weight is similar to that of a KAR (about 50 kDa) and a product whose apparent molecular weight is similar to that of the candidate polypeptide (especially between about 10 and 16 kDa).

This identification method according to the invention can be carried out in particular by:
bringing said antibody into contact as described above,
precipitating the reaction products which may be formed, under mild detergent conditions which preserve the molecular complexes (for example 1% digitonin; cf. Example 1 above),
measuring the molecular weight of the precipitated products, for example by electrophoretic migration in the presence of molecular weight markers on a polyacrylamide gel under denaturing conditions, and
identifying the candidate polypeptide as being a KARAP polypeptide according to the invention as described above.

EXAMPLE 3

1° Identification of Several ESTs Corresponding to KARAP

Our strategy for cloning murine KARAP by biological data processing, as shown in Example 2 above, also reveals the existence of 5 ESTs (Expressed Tag Sequences) which correspond to our definition of KARAP. These are EST AA242315, AA734769, W88159, AA098506 and W41142. FIGS. 10A to 14A illustrate the cDNA sequences of EST AA242315, AA734769, W88159, AA098506 and W41142 respectively (SEQ ID no. 6 to SEQ ID no. 10 respectively). FIGS. 10B to 14B illustrate the protein sequences corresponding respectively to these ESTs (SEQ ID no. 11 to SEQ ID no. 15 for the proteins of EST AA242315, AA734769, W88159, AA098506 and W41142 respectively). All these ESTs were obtained from tissues taken from C57Bl/6 mice and were aligned in order to obtain a cDNA sequence corresponding to an open reading frame. This is illustrated in FIG. 15, which shows the alignment of the sequences of EST AA098506 (SEQ ID no. 9), AA242315 (SEQ ID no. 6), W88159 (SEQ ID no. 8), AA734769 (SEQ ID no. 7) and W41142 (SEQ ID no. 10) and shows the resulting consensus sequence (consensus murine KARAP cDNA; SEQ ID no. 16).

This is also illustrated in FIG. 16, which shows the alignment of the protein sequences of EST AA242315 (SEQ ID no. 11), W88159 (SEQ ID no. 13), W41142 (SEQ ID no. 15), AA098506 (SEQ ID no. 14) and AA734769 (SEQ ID no. 12) and shows the resulting consensus sequence (consensus murine KARAP; SEQ ID no. 17). In these FIGS. 15 and 16, the symbol "." indicates an identity with the consensus sequence in question and the symbol "-" indicates the absence of sequencing data.

2° Genomic Sequence of Murine KARAP

A library of genomic DNA (phage lambda, EMBL3), isolated from mice of the 129 murine line, was screened with the cDNA corresponding to the sequence of EST AA734769 by a conventional technique. A phage containing an 18 kb fragment was identified as positive. This phage was mapped by cleavage with a series of restriction enzymes and a 9 kb EcoRI-EcoRI fragment obtained from the phage was cloned into cloning vector pBlue-Script and contains the whole of the murine KARAP gene (from the initial ATG to the STOP sequence). The sequence of this murine KARAP gene is shown in FIG. 17 (SEQ ID no. 18; 2838 bp).

Furthermore, oligonucleotide primers were generated in order to obtain the genomic organization of murine KARAP. The primers used are shown in Table 1 below (SEQ ID no. 19 to SEQ ID no. 26):

TABLE I

| Identification no. | Strandedness | Position* | Sequence (5'-3') | |
|---|---|---|---|---|
| 7134 | Sense | 60-81 | GGC TCT GGA GCC CTC CTG GTG C | SEQ ID No. 19 |
| 7132 | Antisense | 581-561 | ACT CTG GGC CTG TAC GGG ACT | SEQ ID No. 20 |

TABLE I-continued

| Identification no. | Strandedness | Position* | Sequence (5'-3') | |
|---|---|---|---|---|
| 7133 | Sense | 561-581 | AGT CCC GTA CAG GCC CAG AGT | SEQ ID No. 21 |
| 7130 | Antisense | 800-780 | CAG AGT CAA CAC CAA GTC ACC | SEQ ID No. 22 |
| 7131 | Sense | 780-800 | GGT GAC TTG GTG TTG ACT CTG | SEQ ID No. 23 |
| 7128 | Antisense | 978-958 | CTC AGT CTC AGC AAT GTG TTG | SEQ ID No. 24 |
| 7129 | Sense | 958-978 | CAA CAC ATT GCT GAG ACT GAG | SEQ ID No. 25 |
| 7127 | Antisense | 2703-2683 | CTG TGT GTT GAG GTC ACT GTA | SEQ ID No. 26 |

*Position according to the genomic sequence

The genomic organization of murine KARAP is shown in FIG. 18. We also obtained the cDNA sequence and hence the protein sequence of murine KARAP of the 129 line from these data. This cDNA sequence (SEQ ID no. 27) and this protein sequence (SEQ ID no. 28) are shown in FIG. 19.

The protein sequence translated in this way is:

| | |
|---|---|
| MGALEPSWCLLFLPVLLTVLGLSPVQA | Signal sequence |
| QSDTFPRCDCSSVPG | Extracytoplasmic domain |
| VLAGIVLGDLVLTLLIALAYSLG | Transmembrane domain |
| RLVSRGQERTRKQHIAETESPYQELQGQRPEVYSDLNTQRQYYR | Intracytoplasmic domain |

Considered together, these genomic mapping results show that the murine KARAP gene (from the initial ATG to the STOP sequence) has a length of about 2.9 kb and comprises 5 exons. These results are illustrated in FIG. 20, which shows, from top to bottom, the genomic DNA of murine KARAP of 129 mice (black: translated exon; horizontal hatching: untranslated exon; white: intron), the corresponding protein sequence (SEQ ID no. 28 from exon no. 1 to exon no. 5) and the nature of the different regions of this protein (SS=signal sequence; EC=extracytoplasmic domain; TM=transmembrane domain; IC=intracytoplasmic domain). Exon 1 codes for an N-terminal portion of the signal sequence, exon 2 codes for the remainder of the signal sequence and the first three amino acids of the extracytoplasmic part, exon 3 codes for the remainder of the extracytoplasmic part, the transmembrane part and the first 9 amino acids of the intracytoplasmic part, exon 4 codes for the 14 amino acids of the intracytoplasmic part and exon 5 codes for the remainder of the protein. As expected for the genomic organization of an ITAM polypeptide like KARAP, the ITAM is coded for by two exons (exons 4 and 5) separated by a type 0 intron.

3° Functional Reconstitution of a KAR (p50.2) Expressed in RBL-2H3 Cells by the Human KARAP DAP-12

We obtained the cDNA coding for human KARAP by RT-PCR, generating oligonucleotide primers deduced from the sequence of murine KARAP. The primers used are shown in Table 2 below (SEQ ID no. 29 and no. 30):

TABLE 2

| Identification no. | Strandedness | Location* | Sequence (5'-3') | |
|---|---|---|---|---|
| 7367 | Sense | ATG(53) | CCG<u>CTCGAG</u>GGCTTC<u>ATG</u>GGGGGACTTGAAC<br>Xho I      Start codon | (SEQ ID No. 29) |
| 7368 | Antisense | 398 | CTAG<u>TCTAGA GGATCC</u>AGGTATCATTGTGCTGACTGTCATGATTCG(398)<br>Xba I  Bam III | (SEQ ID No. 30) |

*Numbering as a function of the murine cDNA sequence (SEQ ID No. 27)

The sequence of the cDNA obtained is shown in FIG. 21 (SEQ ID no. 31; cDNA of human KARAP). RNA extracted from KAR+ human NK clones was used as the base for generating this cDNA. This cDNA was cloned into eukaryotic expression vector pNT-neo and stable transfectants for this human KARAP were generated in the KAR+ transfectant (p50.2) of the RBL-2H3 cell line (Bléry et al., J. Biol. Chem., 1997). The capacity of the KARs expressed on the now doubly transfected p50.2+ and KARAP+ RBL-2H3 cells to transduce an activatory signal was tested by stimulation with antibodies directed against the extracytoplasmic part of p50.2 and by following the release of tritiated serotonin.

The protocol adopted for this tritiated serotonin release experiment is as follows:

These cells are detached, centrifuged and resuspended in RPMI/10% FCS at a final concentration of 1×10⁶ cells per ml. The cells are then incubated for 1 hour with 2 μCi of tritium-labelled serotonin per ml of cells. The cells are washed and then reintroduced into medium for 1 hour at 37° C. so that they release the excess serotonin from their stocks. The cells are then distributed into 96-well plates (200,000 cells per well) with mouse IgE (2682-I) or an anti-p50 Ab (GL183). The cells adhere for 1 hour and are then washed. They are returned to 37° C. for 15 minutes and then stimulated with F(ab')2 GAM (50 μg/ml). The cells are left for 30 minutes at 37° C. to enable them to release their serotonin. The reaction is stopped by adding cold HBSS and placing the cells on ice. Half of the supernatant from each well is then recovered and placed in 1 ml of scintillation liquid. 100% degranulation is obtained from the same volume of lyzate obtained from cells which incorporate serotonin but are not stimulated. The samples are then counted on a β counter.

The results obtained are illustrated in FIG. 22, which shows the % of serotonin released into the supernatant by the doubly transfected p50/human KARAP RBL-2H3 cells stimulated by the antibody indicated on the abscissa (left: no antibody; centre: mouse IgE: mIgE 1/500; right: GL183 5 μg/ml). As indicated in this FIG. 22, whereas the uptake of KAR into RBL-2H3 by an antibody reacting with the extracytoplasmic part of KAR (the monoclonal antibody GL183) does not result in activation of the cells, the uptake of KAR by GL183 in the RBL-2H3 double transfectants expressing both human KAR and human KARAP does result in cell activation (objectified here by the release of serotonin from the cells). This is therefore the formal proof that the identified human KARAP sequence reconstitutes the functionality of KARs.

FIG. 23 illustrates the homology between the organization of the human KARAP gene and that of the murine KARAP gene (E1 to E5: exon 1 to exon 5; I1 to I4: intron 1 to intron 4). The numbering of the base pairs of the human and murine KARAP genes is indicated in said Figure.

The invention claimed is:

1. An isolated polypeptide, characterized in that it makes it possible to restore a deficient Killer Cell Activatory Receptor (KAR) activation, in that it is capable of associating with a KAR, and not associating with the inhibitory counterpart of the KAR, and in that its amino acid sequence comprises the amino acid sequence encoded by the nucleic acid sequence represented by SEQ ID NO: 31.

2. A polypeptide according to claim 1, characterized in that said polypeptide is an NK cell polypeptide, or a T cell polypeptide or a myeloid cell polypeptide or a B cell polypeptide or a mastocyte polypeptide.

3. A polypeptide according to claim 1, characterized in that it is phosphorylated at the level of at least one tyrosine residue.

4. A polypeptide according to claim 1, characterized in that it binds to a molecule having a Src Homology 2 (SH2) or Phosphotyrosine Binding (PTB) domain.

5. A polypeptide according to claim 1, characterized in that it binds to a molecule having an SH2 or PTB domain.

6. A polypeptide according to claim 1, characterized in that it is modified by glycosylation, or modified by phosphorylation, or modified by sulphonation, or modified by biotinylation, or modified by acylation or modified by esterification, or modified by the addition of entities whose molecular shape is similar to that of phosphate groups, or modified by the substitution of entities whose molecular shape is similar to that of phosphate groups, or removal of entities whose molecular shape is similar to that of phosphate groups, or modified by the addition of tracer reagents, or modified by the addition of purification targets, or modified by the addition of entities modifying its solubility.

7. A polypeptide according to claim 1, characterized in that it is capable of crossing a cell membrane.

8. A polypeptide according to claim 1, characterized in that it is modified so as to inhibit its capacity to transduce a signal.

9. A polypeptide according to claim 8, characterized in that it is modified so as to be non-hydrolyzable under biological conditions.

10. A polypeptide according to claim 8, characterized in that it is modified by substitution of a tyrosine residue with a phenylalanine residue.

11. A method of identifying candidate molecules which enhance the activation of a KAR, characterized in that it comprises steps involving:
  i) bringing of the candidate molecules into contact with a polypeptide according to claim 1, and
  ii) selection of those candidate molecules for which a binding to said polypeptide is observed, wherein binding to the polypeptide of claim 1 indicates that the candidate molecule is capable of enhancing the activation of a KAR.

12. A method of identifying candidate molecules capable of modulating a cell activity resulting from the activation of a KAR, characterized in that it comprises steps involving:

i) bringing of the candidate molecules into contact with molecules identified by the method according to claim 11, and with said polypeptide, and ii) selection of those candidate molecules which modulate the binding between said polypeptide and a molecule identified by the method of claim 11, as observed in the absence of said candidate molecules wherein candidate molecules which modulate binding of said polypeptide with a molecule identified by the method of claim 11 are capable of modulating a cell activity resulting from the activation of a KAR.

13. A polypeptide according to claim 6, wherein said entities whose molecular shape is similar to that of phosphate groups include a phosphonate, said tracer reagents include luciferase, GFP (Green Fluorescence Protein) or analogues thereof, and said purification targets include an affinity ligand.

14. A polypeptide according to claim 9, wherein said modification includes addition of at least one phosphonate group.

* * * * *